United States Patent
Chakravarty et al.

(10) Patent No.: US 8,710,086 B2
(45) Date of Patent: Apr. 29, 2014

(54) SUBSTITUTED DI-ARYLHYDANTOIN AND DI-ARYLTHIOHYDANTOIN COMPOUNDS AND METHODS OF USE THEREOF

(75) Inventors: Sarvajit Chakravarty, Mountain View, CA (US); Rajendra Parasmal Jain, Pune (IN)

(73) Assignee: Medivation Technologies, Inc., San Francisco, CA (US)

( * ) Notice: Subject to any disclaimer, the term of this patent is extended or adjusted under 35 U.S.C. 154(b) by 0 days.

(21) Appl. No.: 13/263,728

(22) PCT Filed: Apr. 9, 2010

(86) PCT No.: PCT/US2010/030581
§ 371 (c)(1),
(2), (4) Date: Dec. 5, 2011

(87) PCT Pub. No.: WO2010/118354
PCT Pub. Date: Oct. 14, 2010

(65) Prior Publication Data
US 2012/0184580 A1    Jul. 19, 2012

Related U.S. Application Data

(60) Provisional application No. 61/173,438, filed on Apr. 28, 2009.

(30) Foreign Application Priority Data

Apr. 9, 2009    (IN) .............................. 731/DEL/2009

(51) Int. Cl.
*A61K 31/4439*    (2006.01)
*A61K 31/4166*    (2006.01)
*C07D 403/04*    (2006.01)
*C07D 233/72*    (2006.01)

(52) U.S. Cl.
USPC ...... 514/354; 514/391; 548/314.7; 548/316.7

(58) Field of Classification Search
None
See application file for complete search history.

(56) References Cited

U.S. PATENT DOCUMENTS

| | | | |
|---|---|---|---|
| 6,759,415 B1 | 7/2004 | Poitout et al. | |
| 7,138,421 B2 * | 11/2006 | Cleve et al. | 514/391 |
| 7,601,748 B2 * | 10/2009 | Cleve et al. | 514/391 |
| 7,709,517 B2 * | 5/2010 | Sawyers et al. | 514/392 |
| 8,110,594 B2 * | 2/2012 | Jung et al. | 514/391 |
| 8,183,274 B2 * | 5/2012 | Sawyers et al. | 514/391 |
| 2005/0154028 A1 * | 7/2005 | Bromidge et al. | 514/341 |
| 2006/0025589 A1 * | 2/2006 | Binet et al. | 544/139 |
| 2007/0004753 A1 | 1/2007 | Sawyers et al. | |
| 2007/0191443 A1 * | 8/2007 | Jung et al. | 514/385 |
| 2007/0254933 A1 | 11/2007 | Jung et al. | |
| 2008/0139634 A2 * | 6/2008 | Jung et al. | 514/387 |
| 2009/0111864 A1 * | 4/2009 | Jung et al. | 514/391 |
| 2010/0172975 A1 * | 7/2010 | Sawyers et al. | 424/457 |
| 2011/0306615 A1 * | 12/2011 | Tachibana et al. | 514/235.8 |
| 2012/0035231 A1 * | 2/2012 | Jain et al. | 514/391 |
| 2013/0034501 A1 * | 2/2013 | Sawyers et al. | 424/9.2 |

OTHER PUBLICATIONS

Seruga, B., Ocana, Al., Tannock, I. F. Drug resistance in metastatic castration-resistant prostate cancer. Nature Review Clinical Oncology. 2011, 8, 12-23.*

* cited by examiner

*Primary Examiner* — Michael Barker
*Assistant Examiner* — Po-Chih Chen
(74) *Attorney, Agent, or Firm* — Banner & Witcoff, Ltd.

(57) ABSTRACT

Substituted di-arylhydantoin and di-arylthiohydantoins are provided and may find use as androgen receptor modulators. The compounds may find particular use in treating prostate cancer, including CRPC and/or hormone-sensitive prostate cancer.

20 Claims, No Drawings

SUBSTITUTED DI-ARYLHYDANTOIN AND DI-ARYLTHIOHYDANTOIN COMPOUNDS AND METHODS OF USE THEREOF

CROSS-REFERENCE TO RELATED APPLICATIONS

This patent application is submitted under 35 U.S.C. §371 as a U.S. national stage application of International Application No. PCT/US2010/030581, filed on Apr. 9, 2010, which claims priority benefit of U.S. Provisional Patent Application No. 61/173,438, filed Apr. 28, 2009 and entitled "Substituted Di-arylhydantoin and Di-arylthiohydantoin Compounds and Methods of Use Thereof," and of Indian Patent Application No. 731DEL2009, filed Apr.9, 2009 and entitled "Substituted Di-arylhydantoin and Di-arylthiohydantoin Compounds and Methods of Use Thereof," the contents of which are hereby incorporated by reference in their entireties as if they were put forth in full below.

STATEMENT REGARDING FEDERALLY SPONSORED RESEARCH OR DEVELOPMENT

Not applicable.

BACKGROUND OF THE INVENTION

According to the American Cancer Society, prostate cancer is the most commonly diagnosed cancer among men in the United States, other than skin cancer. The American Cancer Society estimates that approximately 186,000 new cases of prostate cancer were diagnosed, and approximately 29,000 men died of prostate cancer, in the United States alone during 2008. Prostate cancer is thus the second-leading cause of cancer death in men in the United States, after lung cancer.

Metastatic prostate cancer is cancer that has spread beyond the prostate and surrounding tissues into distant organs and tissues. The majority of men who die from prostate cancer die from the consequences of metastatic disease. According to the National Cancer Institute, the median survival of patients with prostate cancer that has metastasized to distant organs is usually one to three years, and most such patients will die of prostate cancer. Metastatic prostate cancer is generally divided into two states: the hormone-sensitive state and the castration-resistant state (also referred to as the hormone-refractory state).

Testosterone and other male sex hormones, known collectively as androgens, can fuel the growth of prostate cancer cells. Androgens exert their effects on prostate cancer cells by binding to and activating the androgen receptor, which is expressed in prostate cancer cells. When they first metastasize to distant sites, most prostate cancers depend on androgens for growth. These prostate cancers are known as "hormone-sensitive" cancers. Accordingly, the leading therapies currently used for the treatment of metastatic prostate cancer are focused on diminishing, or antagonizing, the effects of androgens on prostate cancer cells. One approach utilizes so-called "anti-androgens," which are molecules that block the interaction of androgens with the androgen receptor. Another approach is to reduce the amount of androgens produced in the body, primarily in the testes. This can be achieved surgically by removal of both testicles (orchiectomy) or through use of drugs known as luteinizing hormone-releasing hormone, or LHRH, agonist drugs, which lower the native production of testosterone in the testicles (sometimes called "chemical castration").

Most metastatic prostate cancer initially is hormone-sensitive and thus responds to hormonal therapies. However, according to a study published in the Oct. 7, 2004 issue of *The New England Journal of Medicine*, virtually all hormone-sensitive metastatic prostate cancer undergoes changes that convert it to the castration-resistant state in a median of 18-24 months after initiation of hormonal therapy. One of the important mechanisms by which prostate cancer cells switch from the hormone-sensitive to the castration-resistant state appears to be through overexpression of the androgen receptor. In experiments comparing gene expression in hormone-sensitive and castration-resistant prostate cancer cells, an increase in androgen receptor expression was the only gene change consistently associated with castration-resistant disease. Jan. 1, 2004 issue of *Nature Medicine* (Chen C D, Welsbie D S, Tran C et al. Molecular determinants of resistance to antiandrogen therapy. Nat Med 2004; 10(1):33-39). Once in this state, prostate cancers generally continue to grow in an androgen-dependent manner despite the reduction of testosterone production to very low (i.e., post-castration) levels. Prostate cancer in this state is known as "castration-resistant" prostate cancer, or CRPC. The switch from the hormone-sensitive to the castration-resistant state following initiation of hormonal therapy is generally determined based on either rising levels of prostate-specific antigen, or PSA, or documented disease progression as evidenced by imaging tests or clinical symptoms. Metastatic prostate cancer that has become castration-resistant is extremely aggressive; these patients have a median survival of only 10 to 16 months.

A primary reason that CRPC is so deadly is that it is difficult to treat. Because therapies currently used for the treatment of metastatic prostate cancer operate by reducing the ability of androgens to fuel the growth of prostate cancer cells, they generally are effective only on prostate cancers that remain hormone-sensitive by depending on androgens for growth. CRPC no longer responds to hormonal therapies that are effective in the hormone-sensitive state. To further complicate the situation, due to biological changes in prostate cancer that has entered the castration-resistant state, drugs that initially block the androgen receptor and inhibit growth of hormone-sensitive prostate cancer may have precisely the opposite effect and start to fuel the growth of CRPC. For example, Casodex® (bicalutamide), sold by AstraZeneca PLC, directly blocks the interaction of androgens with the androgen receptor and is the largest selling of the anti-androgen therapies. However, in an in vitro model of castration-resistant prostate cancer in which prostate cancer cell lines were genetically engineered to overexpress the androgen receptor (thus converting them from the hormone-sensitive to the castration-resistant state), Casodex® failed effectively to inhibit the androgen receptor in these cells, and in some cases it became a stimulant of the androgen receptor. These findings, which are consistent with the published human clinical experience with Casodex in CRPC, render Casodex® an ineffective therapy for the castration-resistant state of metastatic prostate cancer.

Compounds that bind the androgen receptor, the same target bound by Casodex® and other marketed drugs for metastatic prostate cancer, have been developed for use in the castration-resistant state of metastatic prostate cancer. These compounds bind the androgen receptor in a manner that renders them effective in treating cancers that have become refractory to currently used drugs. For example, certain compounds disclosed in U.S. Patent Application Publication Nos. 2007/0004753, 2007/0254933 and U.S. application Ser. No. 12/257,743 are novel small-molecule androgen receptor antagonists that inhibit androgen receptor function by blocking nuclear translocation of the androgen receptor and DNA binding.

However, there remains an interest in and need for new and alternative therapies for the treatment of prostate cancer. Preferably, new therapies will be effective in treating the hormone-refractory state of metastatic prostate cancer.

BRIEF SUMMARY OF THE INVENTION

Compounds of the formula (I) or salts thereof are provided, as are methods of using the compounds as androgen receptor modulators. Compounds of formula (I) are of the structure:

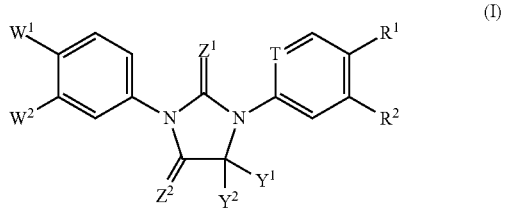

where $W^1$, $W^2$, $Z^1$, $Z^2$, $Y^1$, $Y^2$, T, $R^1$ and $R^2$ are as defined herein. Variations of formula (I) are also provided. Compounds of formula (I) or a variation thereof as detailed herein or a pharmaceutically acceptable salt of any of the foregoing may find particular use in the treatment of prostate cancer, including CRPC and/or hormone-sensitive prostate cancer. Pharmaceutical compositions comprising a compound of formula (I) or a variation thereof as detailed herein or a pharmaceutically acceptable salt of any of the foregoing and a pharmaceutically acceptable carrier are also provided. Compositions of substantially pure compounds are also embraced by the invention. Methods of administering a compound of formula (I) or a variation thereof as detailed herein or a pharmaceutically acceptable salt of any of the foregoing are also provided, as are kits comprising a compound of formula (I) and instructions for use in the treatment of prostate cancer.

DETAILED DESCRIPTION OF THE INVENTION

Definitions

For use herein, unless clearly indicated otherwise, use of the terms "a", "an" and the like refers to one or more.

The term "about" as used herein refers to the usual range of variation for the respective value readily known to the skilled person in this technical field. Reference to "about" a value or parameter herein includes (and describes) embodiments that are directed to that value or parameter per se.

As used herein, the term "androgen receptor modulator" intends and encompasses a compound that binds to or inhibits binding of a ligand to an androgen receptor or reduces or eliminates or increases or enhances or mimics an activity of an adrenergic receptor. As such, an "androgen receptor modulator" encompasses both an androgen receptor antagonist and an androgen receptor agonist. It is possible that an androgen receptor modulator may be an androgen receptor antagonist when utilized in the hormone-sensitive state of prostate cancer and an androgen receptor agonist when utilized in the hormone-refractory state of prostate cancer. In some aspects, the androgen receptor modulator binds to or inhibits binding to a ligand to an androgen receptor. In another aspect, the androgen receptor modulator blocks nuclear translocation of the androgen receptor. In some aspects, the androgen receptor modulator inhibits binding of a ligand to the androgen receptor by at least about or about any one of 10%, 20%, 30%, 40%, 50%, 60%, 70%, 80%, 90%, 95% or 100% as determined in the assays described herein. In some aspects, the androgen receptor modulator reduces an activity of an androgen receptor by at least or about any of 10%, 20%, 30%, 40%, 50%, 60%, 70%, 80%, 90%, 95% or 100% as compared to the corresponding activity in the same subject prior to treatment with the androgen receptor modulator or compared to the corresponding activity in other subjects not receiving the androgen receptor modulator or as determined by other suitable assays. In some aspects, the androgen receptor modulator enhances an activity of an androgen receptor by at least about or about any of 10%, 20%, 30%, 40%, 50%, 60%, 70%, 80%, 90%, 95% or 100 or 200% or 300% or 400% or 500% or more as compared to the corresponding activity in the same subject prior to treatment with the androgen receptor modulator or compared to the corresponding activity in other subjects not receiving the androgen receptor modulator or as determined by other suitable assays. In some aspects, the androgen receptor modulator is capable of binding to the active site of an androgen receptor (e.g., a binding site for a ligand). In some embodiments, the androgen receptor modulator is capable of binding to an allosteric site of an androgen receptor.

Unless clearly indicated otherwise, "an individual" as used herein intends a mammal, including but not limited to a human. The individual may be a male human who has been diagnosed with or is suspected of having a prostate cancer. The individual may be a human who exhibits one or more symptoms associated with prostate cancer. The individual may be a human who has a mutated or abnormal gene associated with prostate cancer. The individual may be a human who is genetically or otherwise predisposed to developing prostate cancer.

As used herein, "treatment" or "treating" is an approach for obtaining beneficial or desired results, including clinical results. For purposes of this invention, beneficial or desired clinical results include, but are not limited to, alleviation of a symptom and/or diminishment of the extent of a symptom and/or preventing a worsening of a symptom associated with prostate cancer. Preferably, treatment of a disease or condition with a compound of the invention or a pharmaceutically acceptable salt thereof is accompanied by no or fewer side effects than are associated with currently available therapies for prostate cancer and/or improves the quality of life of the individual. Treatment may include, but is not limited to, any one or more of: converting an individual from an unfavorable circulating tumor cell count to a favorable circulating tumor cell count, enhancing overall survival time; enhancing progression-free survival time and reducing tumor size.

As used herein, "delaying" development of prostate cancer means to defer, hinder, slow, retard, stabilize and/or postpone development of the disease or condition. This delay can be of varying lengths of time, depending on the history of the disease and/or individual being treated. As is evident to one skilled in the art, a sufficient or significant delay can, in effect, encompass prevention, in that the individual does not develop the disease or condition. For example, a method that "delays" development of CRPC is a method that reduces probability of disease development in a given time frame and/or reduces extent of the disease in a given time frame, when compared to not using the method. Such comparisons are typically based on clinical studies, using a statistically significant number of subjects. Development may also refer to disease progression that may be initially undetectable and includes occurrence, recurrence and onset.

As used herein, an "at risk" individual is an individual who is at risk of developing prostate cancer. An individual "at risk" may or may not have a detectable disease or condition, and may or may not have displayed detectable disease prior to the treatment methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s). These risk factors include, but are not limited to, age, sex, race, diet, history of previous disease, presence of precursor disease, genetic (i.e., hereditary) considerations, and environmental exposure. For example, individuals at risk for CRPC include, e.g., those having metastatic hormone-responsive prostate cancer.

As used herein, the term "effective amount" intends such amount of a compound which in combination with its parameters of efficacy and toxicity, as well as based on the knowledge of the practicing specialist should be effective in a given therapeutic form. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any of the co-administered compounds may optionally be lowered due to the combined action (e.g., additive or synergistic effects) of the compounds.

As used herein, "unit dosage form" refers to physically discrete units, suitable as unit dosages, each unit containing a predetermined quantity of active ingredient calculated to produce the desired therapeutic effect in association with the required pharmaceutical carrier.

As used herein, by "pharmaceutically acceptable" or "pharmacologically acceptable" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

"Pharmaceutically acceptable salts" are those salts which retain at least some of the biological activity of the free (non-salt) compound and which can be administered as drugs or pharmaceuticals to an individual. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Further examples of pharmaceutically acceptable salts include those listed in Berge et al., Pharmaceutical Salts, *J. Pharm. Sci.* 1977 January; 66(1):1-19. Pharmaceutically acceptable salts can be prepared in situ in the manufacturing process, or by separately reacting a purified compound of the invention in its free acid or base form with a suitable organic or inorganic base or acid, respectively, and isolating the salt thus formed during subsequent purification. It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The term "excipient" as used herein means an inert or inactive substance that may be used in the production of a drug or pharmaceutical, such as a tablet containing a compound of the invention as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

"Alkyl" refers to and includes saturated linear, branched, or cyclic hydrocarbon structures and combinations thereof. Particular alkyl groups are those having 1 to 12 carbon atoms (a "$C_1$-$C_{12}$ alkyl"). More particular alkyl groups are those having 1 to 8 carbon atoms (a "$C_1$-$C_8$ alkyl"). When an alkyl residue having a specific number of carbons is named, all geometric isomers having that number of carbons are intended to be encompassed and described; thus, for example, "butyl" is meant to include n-butyl, sec-butyl, iso-butyl, tert-butyl and cyclobutyl; "propyl" includes n-propyl, iso-propyl and cyclopropyl. This term is exemplified by groups such as methyl, t-butyl, n-heptyl, octyl, cyclohexylmethyl, cyclopropyl and the like. Cycloalkyl is a subset of alkyl and can consist of one ring, such as cyclohexyl, or multiple rings, such as adamantyl. A cycloalkyl comprising more than one ring may be fused, spiro or bridged, or combinations thereof. A preferred cycloalkyl has from 3 to 12 annular carbon atoms. A more preferred cycloalkyl has from 3 to 7 annular carbon atoms (a "$C_3$-$C_7$ cycloalkyl"). Examples of cycloalkyl groups include adamantyl, decahydronaphthalenyl, cyclopropyl, cyclobutyl, cyclopentyl and the like.

"Alkenyl" refers to an unsaturated hydrocarbon group having at least one site of olefinic unsaturation (i.e., having at least one moiety of the formula C=C) and preferably having from 2 to 10 carbon atoms and more preferably 2 to 8 carbon atoms. Examples of alkenyl include but are not limited to —$CH_2$—CH=CH—$CH_3$ and —$CH_2$—$CH_2$-cyclohexenyl, where the ethyl group of the later example can be attached to the cyclohexenyl moiety at any available position on the ring.

"Alkynyl" refers to an unsaturated hydrocarbon group having at least one site of acetylenic unsaturation (i.e., having at least one moiety of the formula C≡C) and preferably having from 2 to 10 carbon atoms and more preferably 3 to 8 carbon atoms.

"Substituted alkyl" refers to an alkyl group having from 1 to 5 substituents including, but not limited to, substituents such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkenyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Substituted alkenyl" refers to alkenyl group having from 1 to 5 substituents including, but not limited to, substituents such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Substituted alkynyl" refers to alkynyl groups having from 1 to 5 substituents including, but not limited to, groups such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted heterocyclyl, substituted or unsubstituted aralkyl, aminosulfonyl, sulfonylamino, sulfonyl, oxo, carbonylalkylenealkoxy and the like.

"Aryl" or "Ar" refers to an unsaturated aromatic carbocyclic group having a single ring (e.g., phenyl) or multiple condensed rings (e.g., naphthyl or anthryl). In one variation, the aryl group contains from 6 to 14 annular carbon atoms.

"Heteroaryl" or "HetAr" refers to an unsaturated aromatic carbocyclic group having from 2 to 10 annular carbon atoms and at least one annular heteroatom, including but not limited to heteroatoms such as nitrogen, oxygen and sulfur. A heteroaryl group may have a single ring (e.g., pyridyl, furyl) or multiple condensed rings (e.g., indolizinyl, benzothienyl).

"Substituted aryl" refers to an aryl group having 1 to 5 substituents including, but not limited to, groups such as alkoxy, substituted alkoxy, acyl, acyloxy, carbonylalkoxy, acylamino, substituted or unsubstituted amino, aminoacyl, aminocarbonylamino, aminocarbonyloxy, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Substituted heteroaryl" refers to a heteroaryl group having 1 to 5 substituents including, but not limited to, groups such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Aralkyl" refers to a residue in which an aryl moiety is attached to an alkyl residue and wherein the aralkyl group may be attached to the parent structure at either the aryl or the alkyl residue. Preferably, an aralkyl is connected to the parent structure via the alkyl moiety.

"Aralkenyl" refers to a residue in which an aryl moiety is attached to an alkenyl residue and wherein the aralkenyl group may be attached to the parent structure at either the aryl or the alkenyl residue. Preferably, an aralkenyl is connected to the parent structure via the alkenyl moiety.

"Aralkynyl" refers to a residue in which an aryl moiety is attached to an alkynyl residue and wherein the aralkynyl group may be attached to the parent structure at either the aryl or the alkynyl residue. Preferably, an aralkynyl is connected to the parent structure via the alkynyl moiety.

"Heteroaralkyl" refers to a residue in which a heteroaryl moiety is attached to an alkyl residue and wherein the heroaralkyl group may be attached to the parent structure at either the heroaryl or the alkyl residue. Preferably, a heteroaralkyl is connected to the parent structure via the alkyl moiety.

"Heterocycle", "heterocyclic", or "heterocyclyl" refers to a saturated or an unsaturated non-aromatic group having a single ring or multiple condensed rings, and having from 1 to 10 annular carbon atoms and from 1 to 4 annular heteroatoms, such as nitrogen, sulfur or oxygen. A heterocycle comprising more than one ring may be fused, spiro or bridged, or any combination thereof.

"Substituted heterocyclic" or "substituted heterocyclyl" refers to a heterocycle group which is substituted with from 1 to 3 substituents including, but not limited to, substituents such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted aralkyl, aminosulfonyl, sulfonylamino, sulfonyl, oxo, carbonylalkylenealkoxy and the like. In one variation, a substituted heterocycle is a heterocycle substituted with an additional ring, wherein the additional ring may be aromatic or non-aromatic.

"Halo" or "halogen" refers to elements of the Group 17 series having atomic number 9 to 85. Preferred halo groups include the radicals of fluorine, chlorine, bromine and iodine. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halogen; thus 4-chloro-3-fluorophenyl is within the scope of dihaloaryl. Similarly, a "haloalkenyl" or "haloalkynyl" indicates an alkyl moiety in which at least one H is replaced with a halo group. An alkyl group in which each H is replaced with a halo group is referred to as a "perhaloalkyl." A preferred perhaloalkyl group is trifluoroalkyl ($-CF_3$).

Compounds

Compounds are detailed herein, including in the Brief Summary of the Invention and the appended claims. Use of the detailed compounds, including any and all stereoisomers, salts and solvates thereof, are contemplated in the described methods, e.g., as androgen receptor modulators. Further methods of using the compounds of the invention are detailed throughout.

The invention embraces compounds of the formula (I):

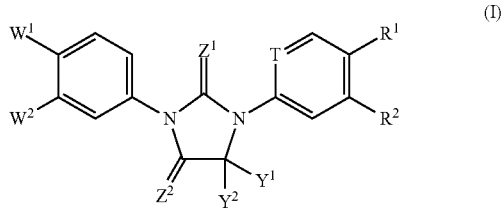

(I)

wherein:
  $W^1$ is CN, $NO_2$ or $SO_2R^4$;
  $W^2$ is alkyl, substituted alkyl, alkenyl, substituted alkenyl, alkynyl, substituted alkynyl or halogen;
  $Z^1$ is S or O
  $Z^2$ is S, O or $NR^4$;
  $Y^1$ and $Y^2$ are independently hydrogen, alkyl, substituted alkyl, alkenyl, substituted alkenyl, alkynyl, substituted alkynyl, aryl, substituted aryl, heteroaryl, substituted heteroaryl, arylalkyl, arylalkenyl, arylalkynyl, heteroaralkyl, heterocyclyl, substituted heterocyclyl or $Y^1$ and $Y^2$ are connected to form a cycle which can be heterocyclic, substituted heterocyclic, cycloalkyl, substituted cycloalkyl;
  T is carbon or nitrogen and can be at any position in the ring;
  $R^1$ is $-C_1-C_8$alkyl-$NR^aR^b$, $-O-C_1-C_8$alkyl-$NR^cR^d$ or $-C(O)NR^eR^f$,
    where:
      $R^a$ is a $C_2-C_{12}$alkyl and $R^b$ is H or a $C_1-C_{12}$alkyl or $R^a$ and $R^b$ are taken together with the N to which they are attached to form a heterocyclic ring;
      $R^c$ is a $C_1-C_{12}$alkyl and $R^c$ is H or a $C_1-C_{12}$alkyl or $R^c$ and $R^d$ are taken together with the N to which they are attached to form a heterocyclic ring;
      $R^e$ is a $C_2-C_{12}$alkyl and $R^f$ is H or a $C_1-C_{12}$alkyl, or
      $R^e$ is a $C_1-C_{12}$alkyl and $R^f$ is $C_1-C_{12}$alkyl, or
      $R^e$ and $R^f$ are taken together with the N to which they are attached to form a heterocyclic ring;

$R^2$ is hydrogen, halogen, nitro, alkyl and substituted alkyl and
$R^4$ is independently H, alkyl, aryl,
or a salt thereof. In one aspect, the salt is a pharmaceutically acceptable salt.

In one variation, the compound is of the formula (I) where $W^1$ is CN. In a further variation, $W^2$ is alkyl, substituted alkyl, alkenyl, substituted alkenyl, alkynyl or substituted alkynyl. In another variation of formula (I), $W^2$ is substituted alkyl, substituted alkenyl or substituted alkynyl where the alkyl, alkenyl or alkynyl is substituted with a halogen. $W^2$ in one aspect is a haloalkyl, haloalkenyl, haloalkynyl or perhaloalkyl. $W^2$ in one aspect is a substituted alkyl. In another variation of formula (I), $W^2$ is substituted alkyl where the alkyl is substituted with a halogen. In one variation of formula (I), $W^2$ is a haloalkyl or perhaloalkyl. In another variation of formula (I), $W^2$ is a perhaloalkyl. The perhaloalkyl in one variation is a $C_1-C_8$ perhaloalkyl, such as trihalomethyl. In one such variation, $W^2$ is trifluoromethyl. In a particular variation of formula (I), $W^1$ is CN and $W^2$ is perhaloalkyl. In another particular variation of formula (I), $W^1$ is CN and $W^2$ is $CF_3$.

In one variation of formula (I), $Y^1$ and $Y^2$ are both a $C_1-C_8$ alkyl. In one such variation, $Y^1$ and $Y^2$ are the same $C_1-C_8$ alkyl, such as when both $Y^1$ and $Y^2$ are methyl, ethyl, propyl or butyl. In one variation of formula (I), $Y^1$ and $Y^2$ are both methyl or are taken together with the carbon to which they are attached to form a $C_4-C_5$ cycloalkyl. In one aspect, compounds of formula (I) are provided where $Y^1$ and $Y^2$ are both methyl. In one variation, compounds of formula (I) are provided where at least one of $Y^1$ and $Y^2$ is alkyl where the alkyl is a cycloalkyl. In another variation, compounds of formula (I) are provided where at least one of $Y^1$ and $Y^2$ is substituted alkyl where the substituted alkyl is a substituted cycloalkyl. In a particular variation, compounds of formula (I) are provided where one or both of $Y^1$ and $Y^2$ are substituted alkyl, substituted alkenyl or substituted alkynyl where the alkyl, alkenyl or alkynyl is substituted with a halogen. In one such variation, at least one of $Y^1$ and $Y^2$ is a haloalkyl, haloalkenyl or haloalkynyl. In another such variation, both $Y^1$ and $Y^2$ are a haloalkyl, haloalkenyl or haloalkynyl. In another aspect, compounds of formula (I) are provided where $Y^1$ and $Y^2$ are taken together with the carbon to which they are attached to form a $C_4-C_5$ cycloalkyl. In one such variation, $Y^1$ and $Y^2$ are taken together to form a cyclobutyl moiety. In a particular of formula (I), $Y^1$ and $Y^2$ are both methyl, $W^1$ is CN. In another particular of formula (I), $Y^1$ and $Y^2$ are both methyl and $W^2$ is a perhaloalkyl such as $CF_3$. In still another variation of formula (I), $Y^1$ and $Y^2$ are both methyl, $W^1$ is CN and $W^2$ is a perhaloalkyl such as $CF_3$.

In one aspect, compounds of formula (I) are provided where $Z^1$ and $Z^2$ are independently S or O. In one variation of formula (I), $Z^1$ is S and $Z^2$ is O. In a particular variation of formula (I), $Z^1$ and $Z^2$ are independently S or O and $Y^1$ and $Y^2$ are both a $C_1-C_8$ alkyl. In one such variation, $Z^1$ is S, $Z^2$ is O and $Y^1$ and $Y^2$ are the same $C_1-C_8$ alkyl. In another variation of formula (I), $Z^1$ and $Z^2$ are independently S or O and $Y^1$ and $Y^2$ are both methyl or are taken together with the carbon to which they are attached to form a $C_4-C_5$ cycloalkyl. In one variation, compounds of formula (I) are provided where $Z^1$ is S, $Z^2$ is O and the compound is further defined by one or more of the following structural features: (i) $Y^1$ and $Y^2$ are both a $C_1-C_8$ alkyl; (ii) $W^1$ is CN; (iii) $W^2$ is perhaloalkyl. In one such variation, compounds of the formula (I) are provided where $Z^1$ is S, $Z^2$ is O, $Y^1$ and $Y^2$ are the same $C_1-C_8$ alkyl, $W^1$ is CN and $W^2$ is $CF_3$.

In one variation of formula (I), T is C. In another variation of formula (I), T is N. It is understood that where applicable, any variation of formula (I) may in one aspect be further defined by T being C. It is understood that where applicable, any variation of formula (I) may in one aspect be further defined by T being N. For example, the variations of the preceding paragraphs may in one aspect be further defined by T being C. Additionally, it is understood that the variations of the preceding paragraphs may in another aspect be further defined by T being N.

Compounds of formula (I) are provided where $R^1$ is $-C_1$-$C_8$ alkyl-$NR^aR^b$ where $R^a$ is a $C_2$-$C_{12}$ alkyl and $R^b$ is H or a $C_1$-$C_{12}$ alkyl or $R^a$ and $R^b$ are taken together with the N to which they are attached to form a heterocyclic ring. In one aspect, the $-C_1$-$C_8$ alkyl moiety of $-C_1$-$C_8$ alkyl-$NR^aR^b$ is a $-(CH_2)_n$ moiety where n is an integer from 1 to 8. In a particular aspect, n is less than 4. In another aspect, n is 1. In one variation, $R^a$ is a $C_2$-$C_{12}$ alkyl and $R^b$ is H. For example, $R^a$ in one variation is ethyl, propyl, butyl or pentyl and $R^b$ is H. In a particular variation, $R^a$ is a $C_2$-$C_8$ alkyl and $R^b$ is H. In still another variation, $R^a$ is a $C_3$-$C_6$ alkyl and $R^b$ is H. Compounds of formula (I) are also provided where $R^a$ is a $C_2$-$C_{12}$ alkyl and $R^b$ is a $C_1$-$C_{12}$ alkyl. In one variation, $R^a$ is a $C_3$-$C_{12}$ cycloalkyl and $R^b$ is a $C_1$-$C_{12}$ alkyl (e.g., methyl). In another variation, $R^a$ and $R^b$ are independently a $C_2$-$C_8$ alkyl. In one such variation, $R^a$ and $R^b$ are the same $C_2$-$C_{12}$ alkyl, e.g., when both $R^a$ and $R^b$ are ethyl. In still another variation, $R^a$ and $R^b$ are independently a $C_3$-$C_6$ alkyl. In still a further variation, compounds of the formula (I) are provided where $R^a$ and $R^b$ are taken together with the N to which they are attached to form a heterocyclic ring. In one aspect, when $R^a$ and $R^b$ are taken together to form a heterocyclic ring, the ring is a $C_4$-$C_7$ heterocyclic ring. The heterocyclic ring formed by $R^a$, $R^b$ and the N to which they are attached in one variation contains only C and N as annular atoms. In one such variation, the heterocycle contains as annular atoms only C and the N provided when $R^a$ and $R^b$ are taken together with the N to which they are attached. In a particular variation of formula (I), $R^a$ and $R^b$ are taken together with the N to which they are attached to form a pyrrolidinyl or piperidinyl ring. Where applicable, for any variation of formula (I) detailed herein wherein $R^1$ is $-C_1$-$C_8$alkyl-$NR^aR^b$, in a particular aspect, the $C_1$-$C_8$ alkyl moiety of $-C_1$-$C_8$ alkyl-$NR^aR^b$ is a $-(CH_2)_n$ moiety where n is 1. Thus, $R^1$ in one variation is $-CH_2NR^aR^b$ where $R^a$ and $R^b$ may be as defined herein. In a particular aspect, $R^1$ is:

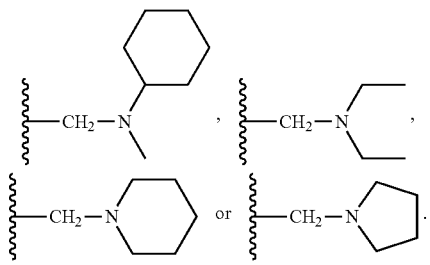

Compounds of the formula (I) where $R^1$ is as detailed in this paragraph may be taken together with the variations noted above for $W^1$, $W^2$, $Z^1$, $Z^2$, $Y^1$, $Y^2$ and T. For example, in one variation the compound is of the formula (I) where $R^1$ is as detailed in this paragraph and the compound is further defined by any one or more of the following structural features: (i) $W^1$ is CN; (ii) $W^2$ is perhaloalkyl (e.g., $CF_3$); (iii) $Z^1$ is S; (iv) $Z^2$ is O; (v) $Y^1$ and $Y^2$ are both methyl and (vi) T is C.

Compounds of formula (I) are provided where $R^1$ is $-O-C_1$-$C_8$ alkyl-$NR^cR^d$ where $R^c$ is a $C_1$-$C_{12}$ alkyl and $R^d$ is H or a $C_1$-$C_{12}$ alkyl or $R^c$ and $R^d$ are taken together with the N to which they are attached to form a heterocyclic ring. In one aspect, the $-C_1$-$C_8$ alkyl moiety of $-O-C_1$-$C_8$ alkyl-$NR^cR^d$ is a $-(CH_2)_n$ moiety where n is an integer from 1 to 8. In a particular aspect, n is less than 4. In another aspect, n is 2. In one variation, $R^c$ is a $C_1$-$C_{12}$alkyl and $R^d$ is H. For example, $R^c$ in one variation is methyl, ethyl, propyl, butyl or pentyl and $R^d$ is H. In a particular variation, $R^c$ is a $C_1$-$C_8$ alkyl and $R^d$ is H. In still another variation, $R^c$ is a $C_1$-$C_4$ alkyl and $R^d$ is H. Compounds of formula (I) are also provided where $R^c$ and $R^d$ are independently a $C_1$-$C_{12}$alkyl. In one such variation, $R^c$ and $R^d$ are the same $C_1$-$C_{12}$alkyl, e.g., when both $R^c$ and $R^d$ are methyl. In another variation, $R^c$ and $R^d$ are independently a $C_1$-$C_8$ alkyl. In still another variation, $R^c$ and $R^d$ are independently a $C_1$-$C_4$ alkyl. In still a further variation, compounds of the formula (I) are provided where $R^c$ and $R^d$ are taken together with the N to which they are attached to form a heterocyclic ring. In one aspect, when $R^c$ and $R^d$ are taken together to form a heterocyclic ring, the ring is a $C_4$-$C_7$ heterocyclic ring. The heterocyclic ring formed by $R^c$, $R^d$ and the N to which they are attached in one variation contains only C and N as annular atoms. In one such variation, the heterocycle contains as annular atoms only C and the N provided when $R^c$ and $R^d$ are taken together with the N to which they are attached. In a particular variation of formula (I), $R^c$ and $R^d$ are taken together with the N to which they are attached to form a pyrrolidinyl or piperidinyl ring. Where applicable, for any variation of formula (I) detailed herein wherein $R^1$ is $-O-C_1$-$C_8$ alkyl-$NR^cR^d$, in a particular aspect, the $C_1$-$C_8$ alkyl moiety of $-O-C_1$-$C_8$ alkyl-$NR^cR^d$ is a $-(CH_2)_n$ moiety where n is 2. Thus, $R^1$ in one variation is $-OCH_2CH_2NR^cR^d$ where $R^c$ and $R^d$ may be as defined herein. In a particular aspect, $R^1$ is:

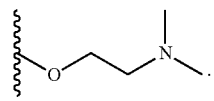 [SMILES: *OCCN(C)C]

Compounds of the formula (I) where $R^1$ is as detailed in this paragraph may be taken together with the variations noted above for $W^1$, $W^2$, $Z^1$, $Z^2$, $Y^1$, $Y^2$ and T. For example, in one variation the compound is of the formula (I) where $R^1$ is as detailed in this paragraph and the compound is further defined by any one or more of the following structural features: (i) $W^1$ is CN; (ii) $W^2$ is perhaloalkyl (e.g., $CF_3$); (iii) $Z^1$ is S; (iv) $Z^2$ is O; (v) $Y^1$ and $Y^2$ are both methyl; (vi) $R^2$ is H, and (vii) T is C.

Compounds of formula (I) are provided where $R^1$ is $-C(O)NR^eR^f$ where $R^e$ and $R^f$ are as defined in provisions (i) or (ii) or (iii): (i) $R^e$ is a $C_2$-$C_{12}$alkyl and $R^f$ is H or a $C_1$-$C_{12}$alkyl; (ii) $R^e$ is a $C_1$-$C_{12}$alkyl and $R^f$ is $C_1$-$C_{12}$alkyl; or (iii) $R^e$ and $R^f$ are taken together with the N to which they are attached to form a heterocyclic ring. In one variation, the compound is of the formula (I) where $R^1$ is $-C(O)NR^eR^f$ and $R^e$ is a $C_2$-$C_{12}$alkyl and $R^f$ is H or a $C_1$-$C_{12}$alkyl. In another variation, the compound is of the formula (I) where $R^1$ is $-C(O)NR^eR^f$ and $R^e$ is a $C_1$-$C_{12}$alkyl and $R^f$ is $C_1$-$C_{12}$alkyl. In still another variation, the compound is of the formula (I) where $R^1$ is $-C(O)NR^eR^f$ and $R^e$ and $R^f$ are taken together with the N to which they are attached to form a heterocyclic ring. In a particular variation, $R^e$ is a $C_2$-$C_{12}$ alkyl and $R^f$ is H. For example, $R^e$ in one variation is ethyl, propyl, butyl, pentyl or hexyl and $R^f$ is H. In another particular variation, $R^e$ is a $C_3-C_{12}$ cycloalkyl (e.g., cyclopentyl) and $R^f$ is H. In a further variation, $R^e$ is a $C_3-C_{12}$ branched alkyl (e.g., tert-butyl) and $R^f$ is H. In a particular variation, $R^e$ is a $C_2-C_8$ alkyl and $R^f$ is H. In still another variation, $R^e$ is a $C_3-C_6$ alkyl and $R^f$ is H. In another particular variation, $R^e$ is a $C_2-C_{12}$ alkyl and $R^f$ is a $C_1-C_{12}$ alkyl (e.g., where $R^e$ is ethyl and $R^f$ is methyl). Compounds of formula (I) are also provided where $R^e$ and $R^f$ are independently a $C_1-C_{12}$ alkyl (e.g., where both $R^e$ and $R^f$ are methyl). In a further variation, compounds of formula (I) are provided where $R^e$ and $R^f$ are independently a $C_2-C_{12}$ alkyl. In one such variation, $R^e$ and $R^f$ are the same $C_2-C_{12}$ alkyl, e.g., when both $R^e$ and $R^f$ are ethyl. In another variation, $R^e$ and $R^f$ are independently a $C_2-C_8$ alkyl. In still another variation, $R^e$ and $R^f$ are independently a $C_3-C_6$ alkyl. In one such variation, at least one of $R^e$ and $R^f$ is a $C_3-C_6$ cycloalkyl. In still a further variation, compounds of the formula (I) are provided where $R^e$ and $R^f$ are taken together with the N to which they are attached to form a heterocyclic ring. In one aspect, when $R^e$ and $R^f$ are taken together to form a heterocyclic ring, the ring is a $C_4-C_7$ heterocyclic ring. The heterocyclic ring formed by $R^e$, $R^f$ and the N to which they are attached in one variation contains only C and N as annular atoms. In one such variation, the heterocycle contains as annular atoms only C and the N provided when $R^e$ and $R^f$ are taken together with the N to which they are attached. In a particular variation of formula (I), $R^e$ and $R^f$ are taken together with the N to which they are attached to form a pyrrolidinyl or piperidinyl ring. In a particular aspect, $R^1$ is:

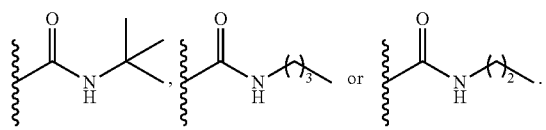

Compounds of the formula (I) where $R^1$ is as detailed in this paragraph may be taken together with the variations noted above for $W^1$, $W^2$, $Z^1$, $Z^2$, $Y^1$, $Y^2$ and T. For example, in one variation the compound is of the formula (I) where $R^1$ is as detailed in this paragraph and the compound is further defined by any one or more of the following structural features: (i) $W^1$ is CN; (ii) $W^2$ is perhaloalkyl (e.g., $CF_3$); (iii) $Z^1$ is S; (iv) $Z^2$ is O; (v) $Y^1$ and $Y^2$ are both methyl and (vi) T is C.

In any variation detailed herein, $R^2$ in one variation is halo (e.g., F). In another variation, $R^2$ is H. In one variation, $R^2$ is halo when $R^1$ is $-C_1-C_8$alkyl-$NR^aR^b$ or $-C(O)NR^eR^f$. In a further variation, $R^2$ is H when $R^1$ is $-O-C_1-C_8$alkyl-$NR^cR^d$.

In a certain variation, the compound of formula (I) has the structure of

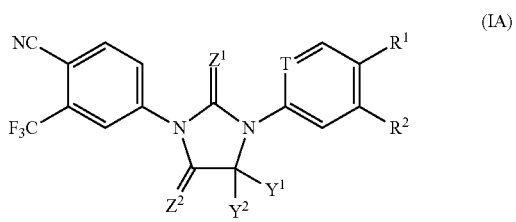

where $Z^1, Z^2, Y^1, Y^2, T, R^1$ and $R^2$ are as defined in formula (I) or any variation thereof.

In another variation, the compound of formula (I) has the structure of

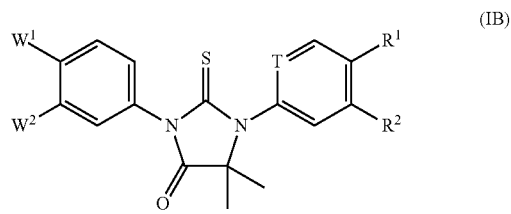

where $W^1$, $W^2$, T, $R^1$ and $R^2$ are as defined in formula (I) or any variation thereof.

In a further variation, the compound of formula (I) has the structure of formula (IC):

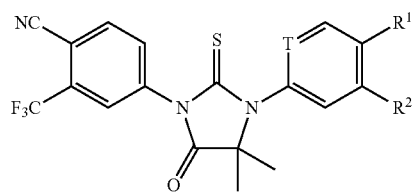

where T, $R^1$ and $R^2$ are as defined in formula (I) or any variation thereof.

In a further variation, the compound of formula (I) has the structure of formula (ID):

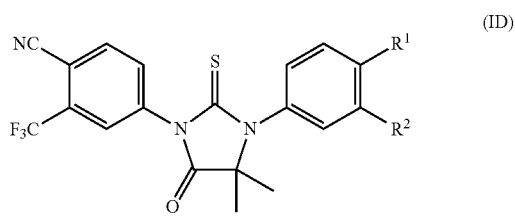

where $R^1$ and $R^2$ are as defined in formula (I) or any variation thereof.

In a further variation, the compound of formula (I) has the structure of

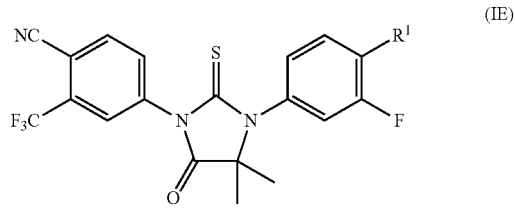

where $R^1$ is as defined in formula (I) or any variation thereof.

In a further variation, the compound of formula (I) has the structure of formula (IF):

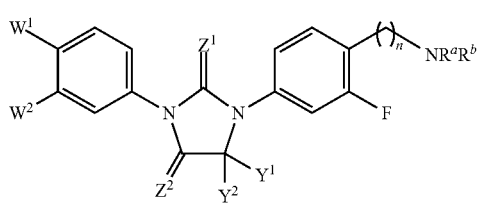

(IF)

where n is an integer from 1 to 8 and $W^1$, $W^2$, $Z^1$, $Z^2$, $Y^2$, $Y^1$, $R^a$ and $R^b$ are as defined in formula (I) or any variation thereof.

In a further variation, the compound of formula (I) has the structure of formula (IG):

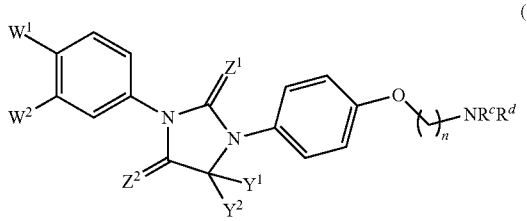

(IG)

where n is an integer from 1 to 8 and $W^1$, $W^2$, $Z^1$, $Z^2$, $Y^2$, $Y^1$, $R^e$ and $R^d$ are as defined in formula (I) or any variation thereof.

In a further variation, the compound of formula (I) has the structure of formula (IH):

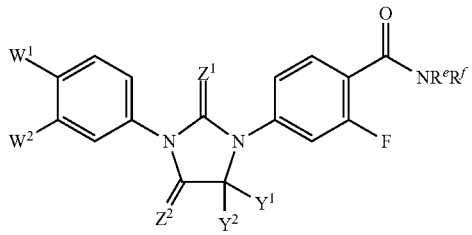

(IH)

where $W^1$, $W^2$, $Z^1$, $Z^2$, $Y^2$, $Y^1$, $R^e$ and $R^f$ are as defined in formula (I) or any variation thereof.

Examples of compounds according to Formula I are depicted in Table 1. The compounds depicted may be present as salts even if salts are not depicted and it is understood that the invention embraces all salts and solvates of the compounds depicted here, as well as the non-salt and non-solvate form of the compound, as is well understood by the skilled artisan. It is thus understood that pharmaceutically acceptable salts of compounds according the invention are intended.

TABLE 1

Representative Compounds of Formula I.

| Structure | Compound No. |
|---|---|
| 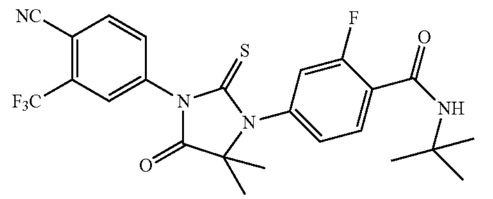 [SMILES: CC(C)(C)NC(=O)c1ccc(N2C(=S)N(c3ccc(C#N)c(C(F)(F)F)c3)C(=O)C2(C)C)cc1F] | 1 |
| 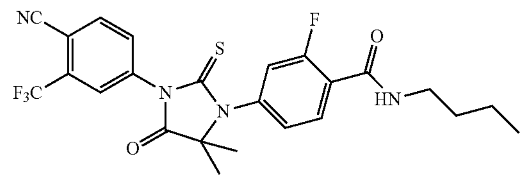 [SMILES: CCCCNC(=O)c1ccc(N2C(=S)N(c3ccc(C#N)c(C(F)(F)F)c3)C(=O)C2(C)C)cc1F] | 2 |
| 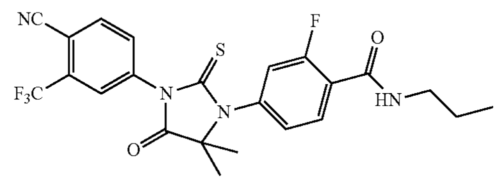 [SMILES: CCCNC(=O)c1ccc(N2C(=S)N(c3ccc(C#N)c(C(F)(F)F)c3)C(=O)C2(C)C)cc1F] | 3 |
| 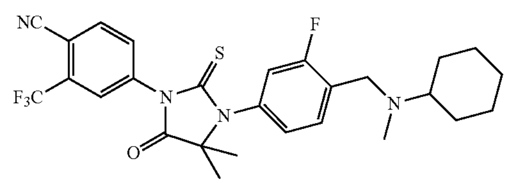 [SMILES: CN(Cc1ccc(N2C(=S)N(c3ccc(C#N)c(C(F)(F)F)c3)C(=O)C2(C)C)cc1F)C1CCCCC1] | 4 |
| 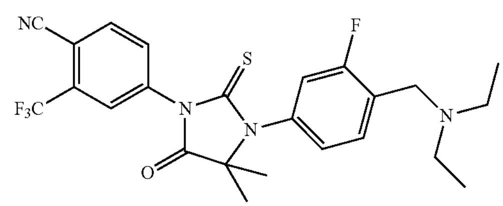 [SMILES: CCN(CC)Cc1ccc(N2C(=S)N(c3ccc(C#N)c(C(F)(F)F)c3)C(=O)C2(C)C)cc1F] | 5 |
| 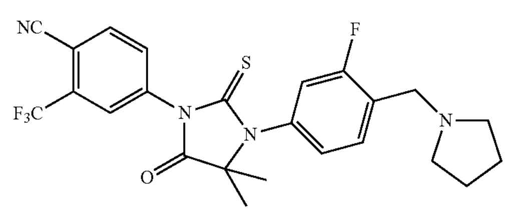 [SMILES: CC1(C)C(=O)N(c2ccc(C#N)c(C(F)(F)F)c2)C(=S)N1c1ccc(CN2CCCC2)c(F)c1] | 6 |
| 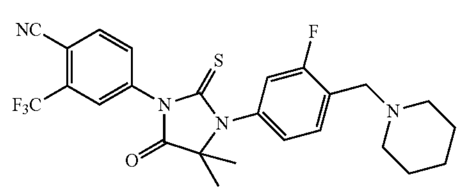 [SMILES: CC1(C)C(=O)N(c2ccc(C#N)c(C(F)(F)F)c2)C(=S)N1c1ccc(CN2CCCCC2)c(F)c1] | 7 |

TABLE 1-continued

Representative Compounds of Formula I.

| Structure | Compound No. |
|---|---|
| [Structure: NC and F3C substituted phenyl attached to imidazolidinone with thione, linked to benzamide with HN-propyl] | 8 |

Pharmaceutical compositions of any of the compounds detailed herein are embraced by this invention. Thus, the invention includes pharmaceutical compositions comprising a compound of the invention or a pharmaceutically acceptable salt thereof and a pharmaceutically acceptable carrier or excipient. Pharmaceutical compositions according to the invention may take a form suitable for oral, buccal, parenteral, nasal, topical or rectal administration, or a form suitable for administration by inhalation.

Compositions comprising a compound of formula (I), or any variation thereof, or a salt the foregoing are provided, such as compositions of substantially pure compounds. In some embodiments, a composition containing a compound of formula (I), (IA), (IB), (IC), (ID), (IE), (IF), (IG) or (IH) or a salt of the foregoing is in substantially pure form. Unless otherwise stated, "substantially pure" intends a composition that contains no more than 35% impurity. For example, with reference to a composition of substantially pure compound 1 from Table 1, the composition may contain no more than 35% of a compound other than compound 1 or a salt thereof. In one variation, a composition of substantially pure compound of the formula (I), (IA), (IB), (IC), (ID), (IE), (IF), (IG) or (IH) or a salt of the foregoing is provided wherein the composition contains no more than 25% impurity. In another variation, a composition of substantially pure compound of the formula (I), (IA), (IB), (IC), (ID), (IE), (IF), (IG) or (IH) or a salt of the foregoing is provided wherein the composition contains or no more than 20% impurity. In still another variation, a composition of substantially pure compound of the formula (I), (IA), (IB), (IC), (ID), (IE), (IF), (IG) or (IH) or a salt of the foregoing is provided wherein the composition contains or no more than 10% impurity. In a further variation, a composition of substantially pure compound of the formula (I), (IA), (IB), (IC), (ID), (IE), (IF), (IG) or (IH) or a salt of the foregoing is provided wherein the composition contains or no more than 5% impurity. In another variation, a composition of substantially pure compound of the formula (I), (IA), (IB), (IC), (ID), (IE), (IF), (IG) or (IH) or a salt of the foregoing is provided wherein the composition contains or no more than 3% impurity. In still another variation, a composition of substantially pure compound of the formula (I), (IA), (IB), (IC), (ID), (IE), (IF), (IG) or (IH) or a salt of the foregoing is provided wherein the composition contains or no more than 1% impurity. In a further variation, a composition of substantially pure compound of the formula (I), (IA), (IB), (IC), (ID), (IE), (IF), (IG) or (IH) or a salt of the foregoing is provided wherein the composition contains or no more than 0.5% impurity.

Unit dosage forms of a compound of the formula (I), (IA), (IB), (IC), (ID), (IE), (IF), (IG) or (IH) or a salt of the foregoing is also provided.

Also provided are kits comprising a compound as detailed herein and instructions for use in the treatment of prostate cancer.

General Description of Biological Assays

The binding properties of compounds disclosed herein to the androgen receptor may be determined. Binding properties may be assessed by methods known in the art, such as competitive binding assays. In one variation, compounds are assessed by the binding assays detailed herein. Compounds disclosed herein may also be tested in cell-based assays or in in vivo models for further characterization. In one aspect, compounds disclosed herein are of any formula detailed herein and further inhibit the binding of a ligand to an androgen receptor. In another aspect, compounds disclosed herein are of any formula detailed herein and further exhibit agonist activity to an androgen receptor. In another aspect, compounds disclosed herein are of any formula detailed herein and further exhibit antagonist agonist activity to an androgen receptor. In another aspect, compounds disclosed herein are of any formula detailed herein and further exhibit efficacy in a preclinical model of prostate cancer, such as CRPC. In another aspect, compounds disclosed herein are of any formula detailed herein and further exhibit efficacy in a preclinical model of prostate cancer, such as hormone-sensitive prostate cancer.

In one variation, inhibition of binding of a ligand to a receptor is measured in the assays described herein. In another variation, inhibition of binding of a ligand is measured in an assay known in the art. In one variation, binding of a ligand to a receptor is inhibited by at least about 80% as determined in a suitable assay known in the art such as the assays described herein. In one variation, binding of a ligand to a receptor is inhibited by greater than about any one of 80%, 85%, 90%, 95%, 100%, or between about 85-95% or between about 90-100% as determined in a suitable assay known in the art such as the assays described herein. In one variation, binding of a ligand to a receptor is inhibited by at least about 80%±20% as determined in an assay known in the art.

Overview of the Methods

The compounds described herein may be used to treat, prevent, delay the onset and/or delay the development of prostate cancer in male humans. A method of treating metastatic prostate cancer in a human male in need thereof is provided, wherein the method comprises administering to the human male an effective amount of a compound of formula (I) or salt thereof or any variation of the foregoing. In one aspect, the compounds described herein may be used to treat, prevent, delay the onset and/or delay the development of CRPC. In another aspect, the compounds described herein may be used to treat, prevent, delay the onset and/or delay the development of hormone-sensitive prostate cancer.

A method of blocking nuclear translation of an androgen receptor in an individual in need thereof is provided, comprising administering to the individual an effective amount of a compound as detailed herein. A method of both binding an androgen receptor and preventing its nuclear translation in an individual in need thereof is provided, comprising administering to the individual an effective amount of a compound as detailed herein. In one aspect, the individual has CRPC. In another aspect, the individual has hormone-sensitive prostate cancer.

A method of converting an individual from having unfavorable circulating tumor cell count to a favorable circulating tumor cell count is provided, comprising administering to the individual an effective amount of a compound as detailed herein. In one variation, the threshold of 5 circulating tumor cells per 7.5 mL of blood is used to stratify patients into those with favorable (<5 circulating tumor cells per 7.5 mL) versus unfavorable (>5 circulating tumor cells per 7.5 mL) outcomes as described by Shafer et al. (Reference: Shafer et al. CirculatingTumor Cell Analysis in Patients with Progressive Castration-Resistant Prostate Cancer. Clin Cancer Res 2007; 13(7) Apr. 1, 2007). In one variation, the circulating tumor cell is associated with CRPC. In one variation, the circulating tumor cell is associated with hormone-sensitive prostate cancer.

A method of reducing prostate tumor size is provided herein. In one variation, the tumor size is reduced to at least ⅓ its original size or at least ¼ its original size. In another variation, the tumor size is reduced to about ⅓ its original size or to about ¼ its original size. In one aspect, the tumor is associated with CRPC. In one aspect, the tumor is associated with hormone-sensitive prostate cancer. Also provided is a method of increasing apoptosis of prostate cancer cells in an individual in need of such treatment, comprising administering to the individual a compound as detailed here. In some embodiments of the method, the individual in need of such treatment has CRPC.

In one variation, the method involves administering a compound as detailed herein to an individual with prostate cancer who has received treatment for prostate cancer with another therapy but who still has or is suspected of having or is susceptible to developing a recurrence of prostate cancer. Thus, in one aspect, a method of using a compound as detailed herein as an adjuvant therapy is contemplated, where the compound is administered to an individual after the individual has received a different first-line or primary therapy. In one method, a compound of formula (I) or salt thereof or any variation of the foregoing is administered to an individual with metastatic prostate cancer as evidenced, e.g., by imaging tests or clinical symptoms. In one method, a compound of formula (I) or salt thereof or any variation of the foregoing is administered to an individual whose prostate specific antigen levels have increased when comparing their levels at a first time to a second time. In one variation, the difference in time between the first time and the second time is at least one month. In another variation, the difference in time between the first time and the second time is about six months.

A method of using a compound as detailed herein as a first-line therapy against prostate cancer in an individual in need thereof is provided, comprising administering to the individual a compound as detailed here. A method of using a compound as detailed herein as a second-line therapy against prostate cancer in an individual in need thereof is provided, comprising administering to the individual a compound as detailed here.

It is to be understood that methods described herein also encompass methods of administering compositions comprising the compounds of the invention, such as pharmaceutical compositions. Methods of administering compositions of substantially pure compounds for use as therapy is also contemplated.

Compounds may be administered in an effective dose. In one aspect, compounds may be administered in an amount of up to 240 mg/day. Compounds may be administered by oral, subcutaneous, intravenous or intramuscular routes. Doses of 10 mg/day, 20 mg/day, 40 mg/day, 100 mg/day, 200 mg/day, 400 mg/day, 800 mg/day.

General Synthetic Methods

The compounds of the invention may be prepared by a number of processes as generally described below and more specifically in the Examples hereinafter. In the following process descriptions, the symbols when used in the formulae depicted are to be understood to represent those groups described above in relation to formula (I) or a variation thereof unless otherwise indicated.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g. a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

General Method 1

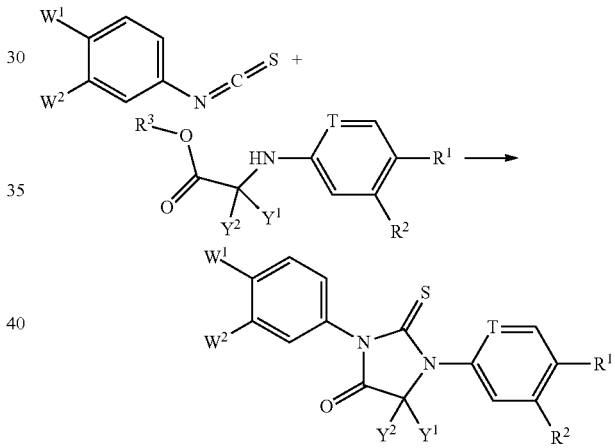

Scheme 1.

General synthetic method 1 is exemplified in scheme 1. A solution of appropriate N-aryl-alpha-amino ester (1 equiv) and appropriate aryl isothiocyanate (1 equiv) in DMSO or DMF or chloroform was heated at 60-100° C. The solvent was removed under reduced pressure and crude material was purified with silica gel chromatography. $R^3$ in General Method 1 is an alkyl, e.g., ethyl or methyl General Method 2

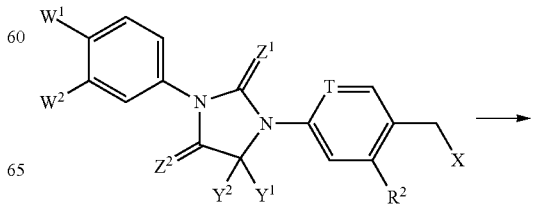

Scheme 2.

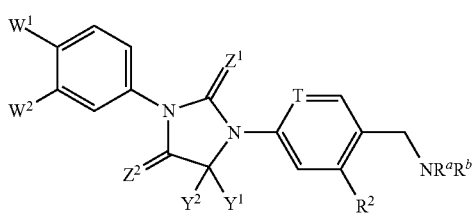

X = Cl, Br or I

General synthetic method 2 is exemplified in scheme 2. To illustrate with a compound where $W^1$ is CN, $W^2$ is $CF_3$, $Z^1$ is S, $Z^2$ is O, $Y^1$ and $Y^2$ are both methyl, T is C and $R^2$ is F, a solution of 4-(3-(4-(chloromethyl)-3-fluorophenyl)-4,4-dimethyl-5-oxo-2-thioxoimidazolidin-1-yl)-2-(trifluoromethyl)benzonitrile (1 equiv) and appropriate amine ($HNR^aR^b$) (3 equiv) in toluene are refluxed for 12 h. The solvent is removed under reduced pressure and the residue was purified by silica gel chromatography.

General Method 3

Scheme 3.

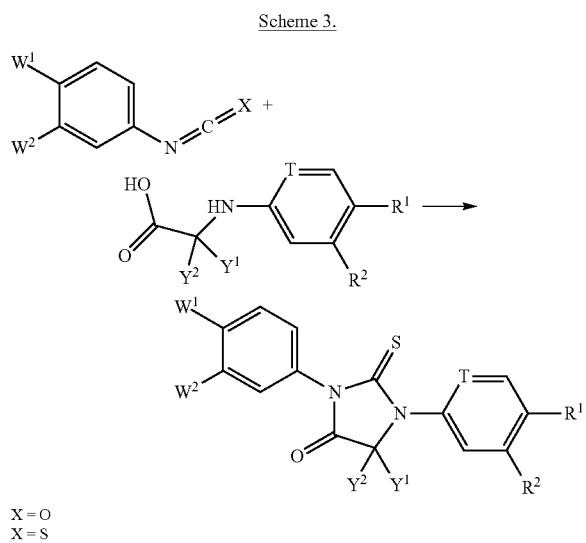

X = O
X = S

General synthetic method 3 is exemplified in scheme 3. A mixture of appropriate N-aryl-alpha-amino acid (1 equiv) and aryl isothiocyanate (1.2 equiv) is heated at 130° C. for 12 h. The reaction mixture is cooled at RT and purified by silica gel chromatography (100-200 mesh) to obtain the product. It is also understood that by utilizing the appropriate $R^1$, this method may also be used to prepare the starting material indicated in General Method 2.

General Method 4

Scheme 4.

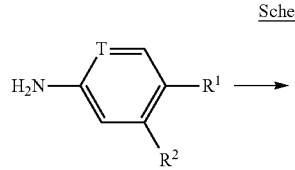

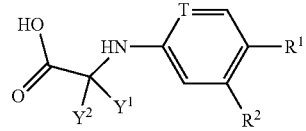

General synthetic method 4 is exemplified in scheme 4 and illustrates methods of making starting materials for use in General Method 3. Taking for example when $Y^1$ and $Y^2$ are both methyl, to a stirred solution of appropriate aromatic amine (1 equiv) in 12 mL dry acetone is added 1,1,1-trichloro-2-methylpropan-2-ol (2.5-3 equiv). It is understood that the reaction may be carried out with other alcohols if $Y^1$ and $Y^2$ are other than methyl. The reaction mixture is cooled to 0° C. Powdered sodium hydroxide is added and the reaction mixture is slowly warmed to room temperature and stirred for at RT for 1 h. The reaction mixture is diluted with diethyl ether and hexane, and filtered to obtain title compound as sodium salt.

General Method 5

Scheme 5.

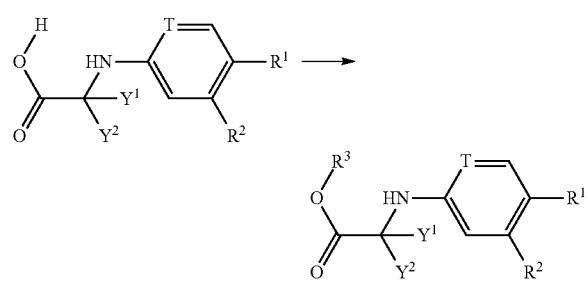

General synthetic method 5 is exemplified in scheme 5 and illustrates methods of making starting materials for use in General Method 1. Taking where $R^3$ is methyl as an example, a solution of N-aryl-alpha-amino acid (1 equiv) and $K_2CO_3$ (2.5-3 equiv) in DMF is stirred at RT for 10 minutes. Methyl iodide (1.5 equiv) is added and the reaction mixture is heated at 55° C. for 4 h. However, it is understood that where $R^3$ is other than methyl, another suitable alkylating agent such as alkyl halide compounds may be used. The solvent is removed under reduced pressure and reaction mixture is poured in to water, extracted with ethyl acetate, dried over $Na_2SO_4$, and concentrated under reduced pressure. The residue is purified by silica gel chromatography.

General Method 6

Scheme 6.

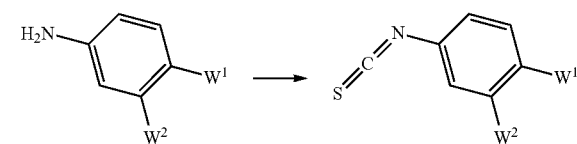

General synthetic method 6 is exemplified in scheme 6 and illustrates methods of making starting materials for use in General Method 1 and 3. A solution of thiophosgene (1.5 equiv) in $H_2O$ is stirred at RT for 15 minutes. Appropriate anilne (1 equiv) was added portion wise and reaction mixture is stirred at RT for 4 h. The reaction mixture is diluted with DCM and washed with H₂O. The organic layer is dried over Na₂SO₄, concentrated under vacuum to obtain aryl isothiocyanate.

General Method 7

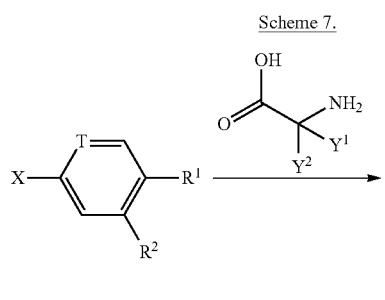

General synthetic method 7 is exemplified in scheme 7 and illustrates a method of making starting materials for use in, e.g., General Method 5. Appropriate aryl halide (1 equiv), appropriate alpha-amino acid (1.5 equiv), CuI (20 mol %), triethylamine (catalytic amount) and K₂CO₃ (3-4 equiv) are dissolved in DMF and water (4:1). The reaction mixture is stirred at RT for 5 min. 2-acetylcyclohexanone (1.1 equiv) is added and the reaction mixture is heated at 100° C. for 18 h. The reaction mixture is acidified with 1 M citric acid (pH 4) and extracted with ethyl acetate. The organic layer is dried over Na₂SO₄ and concentrated to obtain the product.

General Method 8

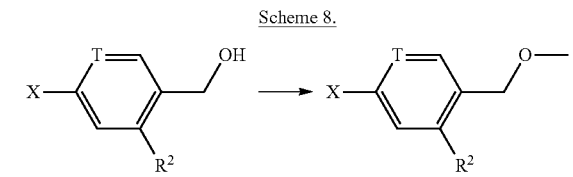

General synthetic method 8 is exemplified in scheme 8. To a suspension of NaH (2.5 equiv) in Dry DMF at 0° C. is added appropriate benzyl alcohol (1 equiv). The reaction mixture is stirred for 15 min. at 0° C. and then warmed to and stirred at RT for 30 min. The reaction mixture is again cooled to 0° C. and MeI (1.5 equiv) is added drop wise. After addition is complete, the reaction mixture is warmed to room temperature and stirred for 1 h. Ice-water is added and the product is extracted with ethyl acetate. The organic layer is dried over anhydrous sodium sulphate, and concentrated under reduced pressure to obtained product.

General Method 9

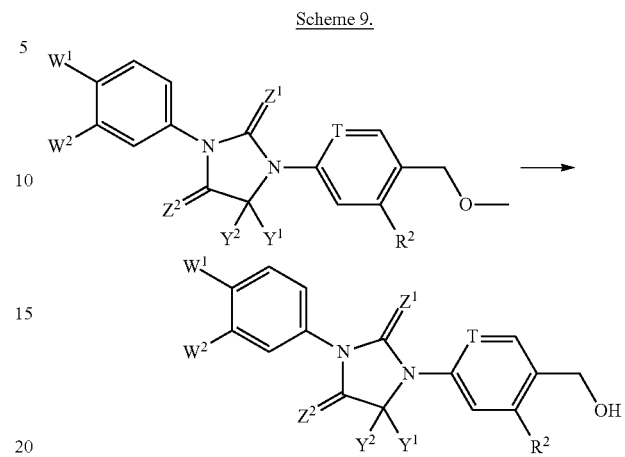

General synthetic method 9 is exemplified in scheme 9. A solution of appropriate methyl ether (1 equiv) is dissolved in DCM and stirred at −70° C. BBr₃ (3 equiv) in DCM is added drop wise at −78° C. and the reaction mixture is allowed to warm to and stirred at RT for 2 h. The reaction mixture is poured in ice and neutralized with saturated NaHCO₃ solution, extracted with ethyl acetate. The organic layer is dried over Na₂SO₄, concentrated under reduced pressure and purified by silica gel chromatography.

General Method 10

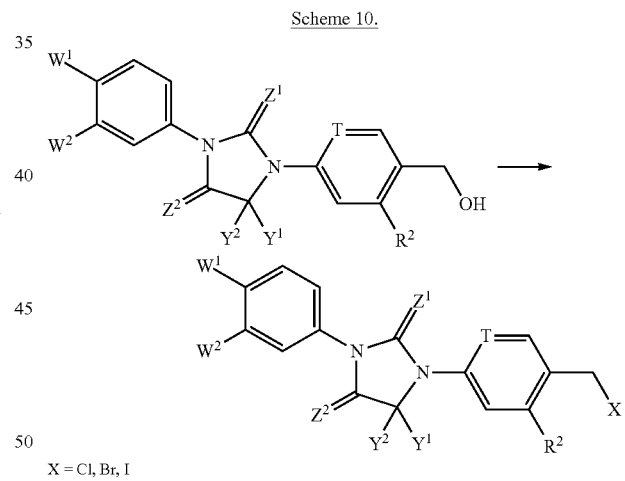

General synthetic method 10 is exemplified in scheme 10. Appropriate aryl methyl alcohol (1 equiv) is dissolved in thionyl chloride (10 fold w/v) and the solution is stirred at 100° C. for 12 h. The reaction mixture is concentrated under reduced pressure to obtain the product.

The methods detailed above may be adapted as known by those of skill in the art. Particular examples of each General Method are provided in the Examples below.

The following abbreviations are used herein: thin layer chromatography (TLC); Hour (h); Ethanol (EtOH); dimethylsulfoxide (DMSO); N,N-dimethylformamide (DMF); trifluoroacetic acid (TFA); tetrahydrofuran (THF); Normal (N); aqueous (aq.); methanol (MeOH); dichloromethane (DCM); Retention factor (Rf).

The following Examples are provided to illustrate but not limit the invention.

All references disclosed herein are incorporated by reference in their entireties.

EXAMPLES

Example 1

Preparation of N-tert-butyl-4-(3-(4-cyano-3-(trifluoromethyl)phenyl)-5,5-dimethyl-4-oxo-2-thioxoimidazolidin-1-yl)-2-fluorobenzamide (Compound 1)

A solution of methyl 2-(4-(tert-butylcarbamoyl)-3-fluorophenylamino)-2-methylpropanoate (50 mg, 0.16 mmol) and 2-(trifluoromethyl)-4-isothiocyanatobenzonitrile (100 mg, 0.43 mmol) in DMSO (1 mL) was heated at 90° C. for 12 h. The reaction mixture was poured in water (10 mL) and extracted with ethyl acetate. The organic layer was dried over $Na_2SO_4$, concentrated under reduced pressure and purified by silica gel chromatography to obtain 5 mg of the product, HPLC, Column: YMC ODS A, 4.6×150 mm, 5 μm, Mobile Phase A: 10 mM Ammonium Acetate, Mobile Phase B: ACN, Gradient: 10% B up to 2 min, 10% B to 90% B in 6 min. hold for 10 min, 90% B to 10% B in 4 min, Flow Rate: 1 mL/min, Retention time: 10.305 min, M+1, 507.

Example 2

Preparation of N-butyl-4-(3-(4-cyano-3-(trifluoromethyl)phenyl)-5,5-dimethyl-4-oxo-2-thioxoimidazolidin-1-yl)-2-fluorobenzamide (Compound 2)

A solution of methyl 2-(4-(butylcarbamoyl)-3-fluorophenylamino)-2-methylpropanoate (50 mg, 0.16 mmol) and 2-(trifluoromethyl)-4-isothiocyanatobenzonitrile (100 mg, 0.43 mmol) in DMSO (1 mL) was heated at 90° C. for 12 h. The reaction mixture was poured in water (10 mL) and extracted with ethyl acetate. The organic layer was dried over $Na_2SO_4$, concentrated under reduced pressure and purified by silica gel chromatography to obtain 7 mg of product, HPLC, Column: YMC ODS AQ, 4.6×250 mm, 5 μm, Mobile Phase A: 10 mM Ammonium Acetate, Mobile Phase B: ACN, Gradient: 10% B up to 2 min, 10% B to 90% B in 6 min. hold for 10 min, 90% B to 10% B in 1 min, Flow Rate: 1 mL/min, Retention time: 10.182 min, M+1, 507.

Example 3

Preparation of 4-(3-(4-cyano-3-(trifluoromethyl)phenyl)-5,5-dimethyl-4-oxo-2-thioxoimidazolidin-1-yl)-2-fluoro-N-propylbenzamide (Compound 3)

A solution of methyl 2-(4-(propylcarbamoyl)-3-fluorophenylamino)-2-methylpropanoate (100 mg, 0.33 mmol) and 2-(trifluoromethyl)-4-isothiocyanatobenzonitrile (115 mg, 0.5 mmol) in DMSO (2.5 mL) was heated at 90° C. for 12 h. The reaction mixture was poured in water (10 mL) and extracted with ethyl acetate. The organic layer was dried over $Na_2SO_4$, concentrated under reduced pressure and purified by silica gel chromatography (100-200) to obtain 4 mg of product, HPLC, Column: YMC ODS A, 4.6×150 mm, 5 μm, Mobile Phase A: 10 mM Ammonium Acetate, Mobile Phase B: ACN, Gradient: 10% to 90% B in 15 min, hold for 3 min. 90% to 10% B in 1 min, Flow Rate: 1 mL/min, Retention time: 16.228 min, M+1, 493

Example 4

Preparation of 4-(3-(4-((cyclohexyl(methyl)amino)methyl)-3-fluorophenyl)-4,4-dimethyl-5-oxo-2-thioxoimidazolidin-1-yl)-2-(trifluoromethyl)benzonitrile (Compound 4)

Compound 4 was prepared according to General Method 2. A solution of 4-(3-(4-(chloromethyl)-3-fluorophenyl)-4,4-dimethyl-5-oxo-2-thioxoimidazolidin-1-yl)-2-(trifluoromethyl)benzonitrile (40 mg, 0.08 mmol) and N-methylcyclohexanamine (30 mg, 0.24 mmol) in toluene 5 mL was refluxed for 12 h. The solvent was removed and residue was purified by silica gel chromatography (eluant: 60% ethyl acetate in hexane) to obtain 7 mg of desired product as brown viscous oil, HPLC, Column: YMC ODS AQ, 4.6×250 mm, 5 μm, Mobile Phase A: 0.05% TFA, Mobile Phase B: ACN, Gradient: 10% to 90% B in 10 min, hold for 10 min. 90% to 10% B in 1 min, Flow Rate: 1 mL/min, Retention time: 9.663 min, M+1, 533

Example 5

Preparation of 4-(3-(4-((diethylamino)methyl)-3-fluorophenyl)-4,4-dimethyl-5-oxo-2-thioxoimidazolidin-1-yl)-2-(trifluoromethyl)benzonitrile (Compound 5)

Compound 5 was prepared according to General Method 2. A solution of 4-(3-(4-(chloromethyl)-3-fluorophenyl)-4,4-dimethyl-5-oxo-2-thioxoimidazolidin-1-yl)-2-(trifluoromethyl)benzonitrile (100 mg, 0.21 mmol) and diethyl amine (48 mg, 0.63 mmol) in toluene 10 mL was refluxed for 12 h. The solvent was removed and residue was purified by silica gel chromatography (eluant: 60% ethyl acetate in hexane) to obtain 32 mg of 4-(3-(4-((diethylamino)methyl)-3-fluorophenyl)-4,4-dimethyl-5-oxo-2-thioxoimidazolidin-1-yl)-2-(trifluoromethyl)benzonitrile as brown viscus oil, HPLC, Column: SUNFIRE C18, 4.6×250 mm, 5 μm, Mobile Phase A: 0.05% TFA, Mobile Phase B: ACN, Gradient: 10% to 90% B in 10 min, hold for 10 min. 90% to 10% B in 1 min, Flow Rate: 1 mL/min, Retention time: 7.43 min, M+1, 493.

Example 6

Preparation of 4-(3-(3-fluoro-4-((pyrrolidin-1-yl)methyl)phenyl)-4,4-dimethyl-5-oxo-2-thioxoimidazolidin-1-yl)-2-(trifluoromethyl)benzonitrile (Compound 6)

Compound 6 was prepared according to General Method 2. A solution of 4-(3-(4-(chloromethyl)-3-fluorophenyl)-4,4-dimethyl-5-oxo-2-thioxoimidazolidin-1-yl)-2-(trifluoromethyl)benzonitrile (100 mg, 0.21 mmol) and pyrrolidine (78 mg, 1.05 mmol) in toluene (10 mL) was refluxed for 12 h. The solvent was removed and residue was purified by silica gel chromatography (eluant: 60% ethyl acetate in hexane) to obtain 13 mg of 4-(3-(3-fluoro-4-((pyrrolidin-1-yl)methyl)phenyl)-4,4-dimethyl-5-oxo-2-thioxoimidazolidin-1-yl)-2-trifluoromethyl)benzonitrile, HPLC, Column: SUNFIRE C18, 4.6×250 mm, 5 μm, Mobile Phase A: 0.05% TFA, Mobile Phase B: ACN, Gradient: 10% to 90% B in 10 min, hold for 10 min. 90% to 10% B in 1 min, Flow Rate: 1 mL/min, Retention time: 7.491 min, M+1, 491.

Example 7

Preparation of 4-(3-(3-fluoro-4-((piperidin-1-yl)methyl)phenyl)-4,4-dimethyl-5-oxo-2-thioxoimidazolidin-1-yl)-2-(trifluoromethyl)benzonitrile (Compound 7)

Compound 7 was prepared according to General Method 2. A solution of 4-(3-(4-(chloromethyl)-3-fluorophenyl)-4,4-dimethyl-5-oxo-2-thioxoimidazolidin-1-yl)-2-(trifluoromethyl)benzonitrile (100 mg, 0.21 mmol) and piperidine (93 mg, 1.05 mmol) in toluene (10 mL) was refluxed for 12 h. The solvent was removed and residue was purified by silica gel chromatography (eluant: 60% ethyl acetate in hexane) to obtain 13 mg of 4-(3-(3-fluoro-4-((piperidin-1-yl)methyl)phenyl)-4,4-dimethyl-5-oxo-2-thioxoimidazolidin-1-yl)-2-(trifluoromethyl)benzonitrile, HPLC, Column: SUNFIRE C18, 4.6×250 mm, 5 μm, Mobile Phase A: 0.05% TFA, Mobile Phase B: ACN, Gradient: 10% to 90% B in 10 min, hold for 10 min. 90% to 10% B in 1 min, Flow Rate: 1 mL/min, Retention time: 7.635 min, M+1, 505.

Example 8

Preparation of 4-(3-(4-(2-(dimethylamino)ethoxy)phenyl)-4,4-dimethyl-5-oxo-2-thioxoimidazolidin-1-yl)-2-(trifluoromethyl)benzonitrile (Compound 8)

Compound 8 was prepared according to General Method 3. A mixture of sodium 2-(4-(2-(dimethylamino)ethoxy)phenylamino)-2-methylpropanoate (107 mg, 0.37 mmol) and 2-(trifluoromethyl)-4-isothiocyanatobenzonitrile (107 mg, 0.44 mmol) was heated at 100° C. for 1 h then 82° C. for 12 h. The crude product was purified by silica gel chromatography using 100-200 Mesh silica gel (10% methanol in DCM) to obtain 30 mg of 4-(3-(4-(2-(dimethylamino)ethoxy)phenyl)-4,4-dimethyl-5-oxo-2-thioxoimidazolidin-1-yl)-2-(trifluoromethyl)benzonitrile. The product was converted its HCl salt by treating with ethanolic HCl, HPLC, Column: HYPERSIL GOLD C18, 4.6×250 mm, 5 μm, Mobile Phase A: 0.05% TFA, Mobile Phase B: ACN, Gradient: 10% to 90% B in 10 min, hold for 10 min. 90% to 10% B in 1 min, Flow Rate: 1 mL/min, Retention time: 9.568 min, M+1, 477.

Example 9

Preparation of intermediate 2-[4-(2-Dimethylamino-ethoxy)-phenylamino]-2-methyl-propionic acid

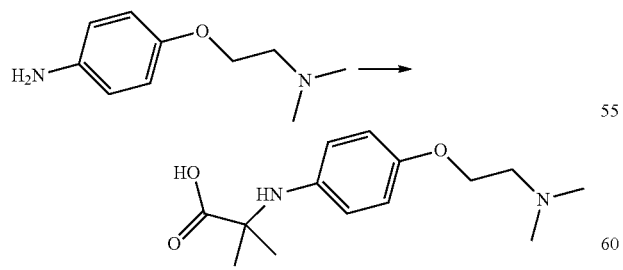

The title compound was prepared according to General Method 4. To a stirred solution of 4-(2-Dimethylamino-ethoxy)-phenylamine (0.2 g, 1.10 mmol) in 12 mL dry acetone was added 1,1,1-trichloro-2-methylpropan-2-ol (0.525 g, 2.9 mmol). The reaction mixture was cooled to 0° C. Powdered sodium hydroxide was added and the reaction mixture was slowly warmed to room temperature and stirred for at RT for 1 h. The reaction mixture was diluted with diethyl ether and hexane, filtered and washed with hexane to obtained sodium salt of 2-[4-(2-Dimethylamino-ethoxy)-phenylamino]-2-methyl-propionic acid (200 mg).

Example 10

Preparation of intermediate methyl 2-(4-(butylcarbamoyl)-3-fluorophenylamino)-2-methylpropanoate

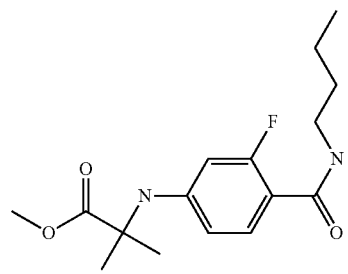 [SMILES: CCCCNC(=O)c1ccc(NC(C)(C)C(=O)OC)cc1F]

The title compound was prepared according to General Method 5. A solution of 2-(4-(butylcarbamoyl)-3-fluorophenylamino)-2-methylpropanoic acid (900 mg, 3.04 mmol) and K₂CO₃ (1.38 mg, 10 mmol) in DMF (10 mL) was stirred at RT for 10 minutes. Methyl iodide (647 mg, 4.5 mmol) was added and heated at 55° C. for 4 h. The solvent was removed and reaction mixture was poured in water, extracted with ethyl acetate (100 mL, 2 times), dried over Na₂SO₄, concentrated and purified with column chromatography to obtain 400 mg of methyl 2-(4-(butylcarbamoyl)-3-fluorophenylamino)-2-methylpropanoate.

Example 11

Preparation of intermediate methyl 2-(4-(tert-butylcarbamoyl)-3-fluorophenylamino)-2-methylpropanoate

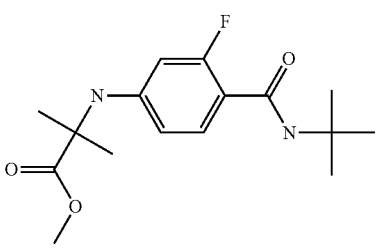 [SMILES: COC(=O)C(C)(C)Nc1ccc(C(=O)NC(C)(C)C)c(F)c1]

The title compound was prepared according to General Method 5. A solution of 2-(4-(tert-butylcarbamoyl)-3-fluorophenylamino)-2-methylpropanoic acid (1.0 g, 3.3 mmol)

and K$_2$CO$_3$ (1.38 g, 10 mmol) in DMF (10 mL) was stirred at RT for 10 minutes. Methyl iodide (710 mg, 5 mmol) was added and heated at 55° C. for 4 h. The solvent was removed and reaction mixture was poured in water, extracted with ethyl acetate (100 mL, 2 times), dried over Na$_2$SO$_4$, concentrated and purified with column chromatography to obtain 300 mg of methyl 2-(4-(tert-butylcarbamoyl)-3-fluorophenylamino)-2-methylpropanoate Example 12

Preparation of intermediate methyl 2-(4-(propylcarbamoyl)-3-fluorophenylamino)-2-methylpropanoate

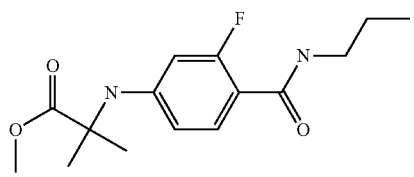 [SMILES: CCCNC(=O)c1ccc(NC(C)(C)C(=O)OC)cc1F]

The title compound was prepared according to General Method 5. A solution of 2-(4-(propylcarbamoyl)-3-fluorophenylamino)-2-methylpropanoic acid (1.0 g, 3.54 mmol) and K$_2$CO$_3$ (1.0 g, 7.2 mmol) in DMF (7 mL) was stirred at RT for 10 minutes. Methyl iodide (0.8 g, 5.6 mmol) was added and heated at 55° C. for 4 h. The solvent was removed and reaction mixture was poured in water, extracted with ethyl acetate, dried over Na$_2$SO$_4$, concentrated and purified with column chromatography to obtain 800 mg of methyl 2-(4-(propylcarbamoyl)-3-fluorophenylamino)-2-methylpropanoate.

Example 13

Preparation of intermediate 2-(trifluoromethyl)-4-isothiocyanatobenzonitrile

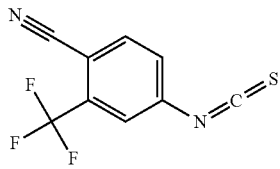 [SMILES: N#Cc1ccc(N=C=S)cc1C(F)(F)F]

The title compound was prepared according to General Method 6. Thiophosgene (10 g, 87.71 mmol) was dissolved in water and stirred at RT for 10 minutes. 4-Amino-2-trifluoromethyl-benzonitrile was added portion wise at RT. The reaction mixture was stirred at RT for 2 h. The product was extracted with dichloromethane, organic layer was washed with water and brine, dried over sodium sulphate and evaporated to obtain 12 g of 4-Isothiocyanato-2-trifluoromethyl-benzonitrile.

Example 14

Preparation of 2-(4-(butylcarbamoyl)-3-fluorophenylamino)-2-methylpropanoic acid

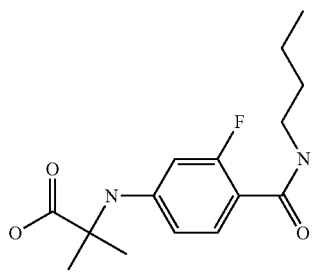 [SMILES: CCCCNC(=O)c1ccc(NC(C)(C)C(=O)O)cc1F]

The title compound was prepared according to General Method 7. 4-bromo-N-butyl-2-fluorobenzamide (950 mg, 3.22 mmol), 2-aminoisobutyric acid (450 mg, 4.36 mmol), CuI (100 mg, 0.5 mmol), TEA (0.1 mL) and K$_2$CO$_3$ (1.0 g, 7.2 mmol) were charged in DMF (8 ml) and water (2 ml) and stirred at RT for 5 min. 2-acetylcyclohexanone (100 mg, 0.7 mmol) was added and the reaction mixture was heated at 100° C. for 18 h. The reaction mixture was acidified with 1 M citric acid (pH 4) and extracted with ethyl acetate (50 mL, 2 times). The combined organic layer was dried over Na$_2$SO$_4$ and concentrated to obtain 900 mg of 2-(4-(butylcarbamoyl)-3-fluorophenylamino)-2-methylpropanoic acid.

Example 15

Preparation of 2-(4-(tert-butylcarbamoyl)-3-fluorophenylamino)-2-methylpropanoic acid

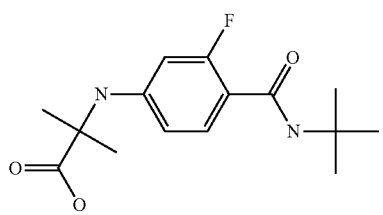 [SMILES: CC(C)(C)NC(=O)c1ccc(NC(C)(C)C(=O)O)cc1F]

The title compound was prepared according to General Method 7. N-tert-butyl-4-bromo-2-fluorobenzamide (850 mg, 3.1 mmol), 2-aminoisobutyric acid (450 mg, 4.36 mmol), CuI (100 mg, 0.5 mmol), TEA (0.2 mL) and K$_2$CO$_3$ (1.0 g, 7.2 mmol) were charged in DMF (8 ml) and water (2 ml) and stirred at RT for 5 min. 2-acetylcyclohexanone (100 mg, 0.7 mmol) was added and the reaction mixture was heated at 100° C. for 18 h. The reaction mixture was acidified with 1 M citric acid (pH 4) and extracted with ethyl acetate (50 mL, 2 times).

The combined organic layer was dried over Na$_2$SO$_4$ and concentrated to obtain 1.0 g of 2-(4-(tert-butylcarbamoyl)-3-fluorophenylamino)-2-methylpropanoic acid.

Example 16

Preparation of 2-(4-(propylcarbamoyl)-3-fluorophenylamino)-2-methylpropanoic acid

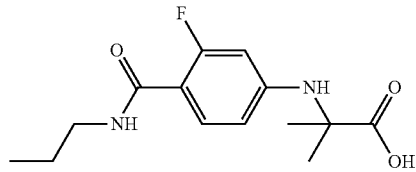 [SMILES: CCCNC(=O)c1ccc(NC(C)(C)C(=O)O)cc1F]

The title compound was prepared according to General Method 7. 4-bromo-2-fluoro-N-propylbenzamide (620 mg, 2.39 mmol), 2-aminoisobutyric acid (422 mg, 4.09 mmol), CuI (100 mg, 0.6 mmol), TEA (catalytic amount) and K$_2$CO$_3$ (1.13 g, 8.1 mmol) were dissolved in DMF (8 ml) and water (2 ml) stirred at RT for 5 min. Then 2-acetylcyclohexanone (0.13 g, 0.3 mmol) was added and the reaction mixture was heated at 100° C. for 18 h. The reaction mixture was acidified with 1 M citric acid (pH 4) and extracted with ethyl acetate (100 mL, 2 times). The combined organic layer was dried over Na$_2$SO$_4$ and concentrated to obtain 1.0 g of 2-(4-(propylcarbamoyl)-3-fluorophenylamino)-2-methylpropanoic acid.

Example 17

Preparation of 4-bromo-2-fluoro-1-(methoxymethyl)benzene

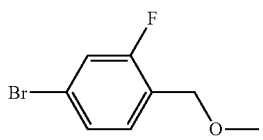

The title compound was prepared according to General Method 8. To a suspension of NaH (50-60% mineral oil, 8 g, 0.33 mol) in Dry DMF (200 mL) at 0° C. was added (4-bromo-2-fluorophenyl)methanol (27 g, 0.1317 mol). The reaction mixture was stirred for 15 min at 0° C. and then warmed to and stirred at RT for 30 min. The reaction mixture was again cooled to 0° C. and MeI (15 mL, 0.1975 mol) was added drop wise. After addition was complete, the reaction mixture was warmed to room temperature and stirred for 1 h. Ice-water was added and the product was extracted with ethyl acetate. The organic layer was dried over anhydrous sodium sulphate, and concentrated under reduced pressure to obtained 4-bromo-2-fluoro-1-(methoxymethyl)benzene (24 g).

Example 18

Preparation of 2-(3-fluoro-4-(methoxymethyl)phenylamino)-2-methylpropanoic acid

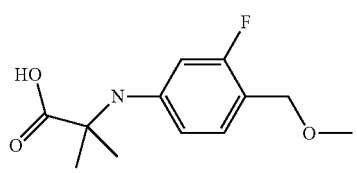 [SMILES: COCc1ccc(NC(C)(C)C(=O)O)cc1F]

The title compound was prepared according to General Method 7. A mixture of 4-bromo-2-fluoro-1-(methoxymethyl)benzene (1 g, 4.5 mmol), 2-aminoisobutiric acid (0.706 g, 6.8 mmol), K$_3$PO$_4$ tribasic (2.4 g, 11.25 mmol), CuI (0.171 g, 0.9 mmol), in water (0.3 mL) and DMF (5 mL) was stirred at RT and TEA (22 mg, 0.2 mmol) and 2-acetylcyclohexanone (118 mg, 0.84 mmol) were added. The reaction mixture was purged with nitrogen and heated at 95° C. for 12 h. The contents were diluted with ice-water and washed with ethyl acetate (20 mL). The aqueous layer was cooled to 0° C. then acidified with 1M citric acid solution (pH 4). The product was extracted with ethyl acetate, the organic layer was dried over anhydrous sodium sulphate, and concentrated under reduced pressure to obtain crude product that was purified by silica gel chromatography (eluant 50% ethyl acetate-hexane) to obtain 2-(3-fluoro-4-(methoxymethyl)phenylamino)-2-methylpropanoic acid (0.7 g).

Example 19

Preparation of methyl 2-(3-fluoro-4-(methoxymethyl)phenylamino)-2-methylpropanoate

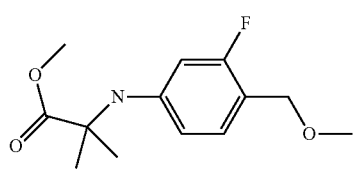 [SMILES: COCc1ccc(NC(C)(C)C(=O)OC)cc1F]

The title compound was prepared according to General Method 5. A mixture of 2-(3-fluoro-4-(methoxymethyl)phenylamino)-2-methylpropanoic acid (1 g, 4.1 mmol), anhydrous K$_2$CO$_3$ (0.858 g, 6.2 mmol) and methyliodide (0.880 g, 6.2 mmol) was stirred at 60° C. for 3 h. The reaction mixture was diluted with water and extracted with ethyl acetate (20 mL×3), organic layer was dried over anhydrous sodium sulfate and concentrated under reduced pressure to obtain crude product that was purified by silica gel chromatography (elu-

33 ant 30% ethyl acetate-hexane) to obtain methyl 2-(3-fluoro-4-(methoxymethyl)phenylamino)-2-methylpropanoate.

Example 20

Preparation of 4-(3-(3-fluoro-4-(methoxymethyl)phenyl)-4,4-dimethyl-5-oxo-2-thioxoimidazolidin-1-yl)-2-(trifluoromethyl)benzonitrile

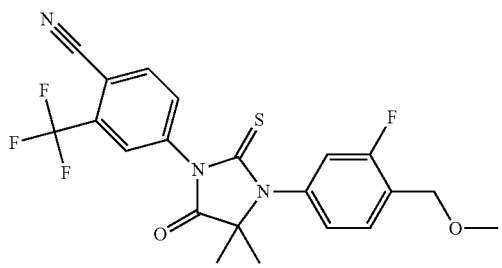 [SMILES: COCc1ccc(N2C(=S)N(c3ccc(C#N)c(C(F)(F)F)c3)C(=O)C2(C)C)cc1F]

The title compound was prepared according to General Method 1. A solution of methyl 2-(3-fluoro-4-(methoxymethyl)phenylamino)-2-methylpropanoate (60 mg, 0.24 mmol) and 2-(trifluoromethyl)-4-isothiocyanatobenzonitrile (120 mg, 0.52 mmol) in DMSO (1 mL) was heated at 82° C. for 12 h. The reaction mixture was poured in water (10 mL) and extracted with ethyl acetate. The organic layer was dried over $Na_2SO_4$, concentrated under reduced pressure and purified by silica gel chromatography (100-200 mesh) to obtain 5 mg of final product, HPLC, Column: YMC ODS AQ, 4.6×250 mm, 5 μm, Mobile Phase A: 0.05% TFA, Mobile Phase B: ACN, Gradient: 10% to 90% B in 10 min, hold for 10 min. 90% to 10% B in 1 min, Flow Rate: 1 mL/min, Retention time: 13.316 min, M+1, 452.

Example 21

Preparation of 4-(3-(3-fluoro-4-(hydroxymethyl)phenyl)-4,4-dimethyl-5-oxo-2-thioxoimidazolidin-1-yl)-2-(trifluoromethyl)benzonitrile

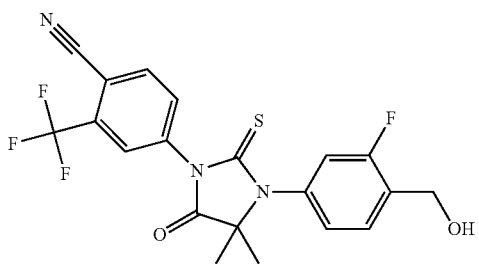 [SMILES: CC1(C)C(=O)N(c2ccc(C#N)c(C(F)(F)F)c2)C(=S)N1c1ccc(CO)c(F)c1]

The title compound was prepared according to General Method 9. A solution of 4-(3-(3-fluoro-4-(methoxymethyl)phenyl)-4,4-dimethyl-5-oxo-2-thioxoimidazolidin-1-yl)-2-(trifluoromethyl)benzonitrile (80 mg, 0.177 mmol) was dissolved in DCM (3 mL) and stirred at −70° C. $BBr_3$ (0.05 mL, 0.54 mmol) in DCM (3 mL) was added drop wise at −78° C. and the reaction mixture was allowed to warm to and stirred at RT for 2 h. The reaction mixture was poured in ice (20 g) and neutralized with saturated $NaHCO_3$ solution, extracted with ethyl acetate (20 mL×2). The organic layer was dried over $Na_2SO_4$, concentrated under reduced pressure and purified by

34 silica gel chromatography to obtain 6 mg of 4-(3-(3-fluoro-4-(hydroxymethyl)phenyl)-4,4-dimethyl-5-oxo-2-thioxoimidazolidin-1-yl)-2-(trifluoromethyl)benzonitrile, HPLC, Column: YMC POLYMER C18, 4.6×150 mm, 5 μm, Mobile Phase A: 0.05% TFA, Mobile Phase B: ACN, Gradient: 10% to 90% B in 15 min, hold for 3 min. 90% to 10% B in 1 min, Flow Rate: 1 mL/min, Retention time: 13.814 min, M+1, 438.

Example 22

Preparation of 4-(3-(4-(chloromethyl)-3-fluorophenyl)-4,4-dimethyl-5-oxo-2-thioxoimidazolidin-1-yl)-2-(trifluoromethyl)benzonitrile

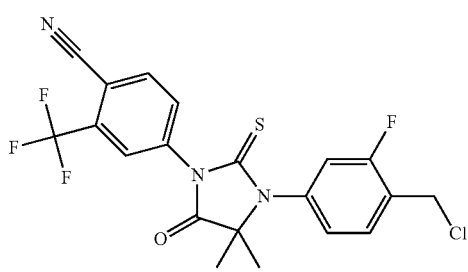 [SMILES: CC1(C)C(=O)N(c2ccc(C#N)c(C(F)(F)F)c2)C(=S)N1c1ccc(CCl)c(F)c1]

The title compound was prepared according to General Method 10. 4-[3-(3-Fluoro-4-hydroxymethyl-phenyl)-4,4-dimethyl-5-oxo-2-thioxo-imidazolidin-1-yl]-2-trifluoromethyl-benzonitrile (0.5 g, 1.14 mmol) was dissolved in thionyl chloride (5 mL) and the solution was stirred at 100° C. for 12 h. The reaction mixture was concentrated under reduced pressure to obtain 300 mg of product.

Example B1

Determination of the Ability of Compounds of the Invention to Bind to the Androgen Receptor The binding assay for evaluating the ability of compounds to interact with the androgen receptor is a filter binding assay that monitors the displacement of a radioactive androgen-binding reference compound ($^3$H-methyltrienolone) from a soluble cytoplasmic androgen receptor preparation obtained from cultured LNCap cells (Liao et al. 1984) J. Steroid. Biochem. 20, 11-17, with modifications). The procedure involves incubating cytoplasmic androgen receptor with $^3$H-methyltrienolone at a concentration of 0.5 nM. Compounds that interact with the androgen receptor displace the radioactive reference compound, reducing the number of radioactive counts bound to the receptor. Remaining $^3$H-methyltrienolone counts are determined by filtration of the sample through a GF/C filter, washing and scintillation counting. Specific ligand binding is defined as the difference between the total binding and non-specific binding determined in the presence of an excess of unlabeled reference compound. The results are expressed as a percent of control specific binding. $IC_{50}$ values (concentration causing a half-maximal inhibition of control specific binding) and Hill coefficients (nH) are determined by non-linear regression analysis of the competition curves generated with mean replicate values using the Hill equation curve fitting $(Y=D+[(A-D)/(1+(C/C_{50})^{nH})]$, where Y=specific binding, D=minimum specific binding, A=maximum specific binding, C=compound concentration, C50=IC50, and nH=slope factor). Inhibition constants (Ki) are calculated using the Cheng Prusoff equation ($K_i = IC_{50}/1+(L/K_D)$), where L=concentration of radioligand in the assay and $K_D$=affinity of the radioligand for the androgen receptor. Certain compounds of the invention were tested in this assay and found to be active, greater than 50% inhibition of ligand binding at 500 nM of test compound.

Example B2

In vitro Activity of Compounds of the Invention in Androgen Receptor Nuclear Translocation Assay (Agonist Format)

The androgen receptor nuclear translocation assay monitors movement of the androgen receptor between the cytoplasmic and nuclear compartments of PathHunter NHRPro cells (DiscoveRX Corporation, Fremont, Calif.). In this assay, an androgen receptor agonist stimulates the translocation of a ProLabel tagged androgen receptor into the nucleus of PathHunter NHRPro cells where it binds to a complementary nuclear EA fragment resulting in the formation of an active β-gal enzyme and production of a chemiluminescent signal upon treatment of the cells with a β-gal substrate. Compounds that act as agonists result in an enhanced chemiluminescent signal within these cells.

In the agonist assay format, PathHunter NHRPro cells are incubated in the presence of varying concentrations of test compound for 5 hours at 37° C. After this incubation period, the PathHunter Detection reagent cocktail is added, followed by a 1 hour incubation at room temperature. A luminescent signal can be read in an appropriate luminometer and reported as relative luminescent units (RLU).

Example B3

In vitro Activity of Compounds of the Invention in Androgen Receptor Nuclear Translocation Assay (Antagonist Format)

Antagonistic properties of compounds are evaluated using the androgen receptor nuclear translocation assay described above. In the antagonist format, PathHunter NHRPro cells are treated with varying concentrations of a reference agonist (trimethylenolone) in order to determine its EC80 value (concentration of reference agonist giving rise to 80% maximum signal). Cells are pretreated with test compound for 1 hour at 37° C. prior to the addition of methyltrienolone agonist at a concentration equal to its EC80 value. Treated cells are further incubated at 37° C. for 5 hours and signal detection was determined as described for the agonist assay.

Example B4

Phase 1, 2 or 3 Human Clinical Studies

Phase 1-2 or 3 clinical trials may be conducted with a compound as detailed herein.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

The invention claimed is:
1. A compound of formula (I):

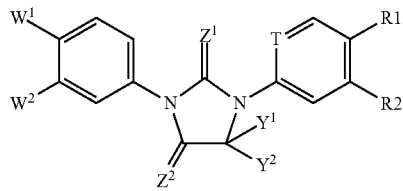

wherein:
$W^1$ is CN, $NO_2$ or $SO_2R^4$;
$W^2$ is alkyl, substituted alkyl, alkenyl, substituted alkenyl, alkynyl, substituted alkynyl or halogen;
$Z^1$ is S or O;
$Z^2$ is S, O or $NR^4$;
$Y^1$ and $Y^2$ are independently hydrogen, alkyl, substituted alkyl, alkenyl, substituted alkenyl, alkynyl, substituted alkynyl, aryl, substituted aryl, heteroaryl, substituted heteroaryl, arylalkyl, arylalkenyl, arylalkynyl, heteroaralkyl, heterocyclyl, or substituted heterocyclyl; or $Y^1$ and $Y^2$ are connected to form a cycle which can be heterocyclic, substituted heterocyclic, cycloalkyl, or substituted cycloalkyl;
T is nitrogen and can be at any position in the ring;
$R^1$ is —O—$C_1C_8$alkyl-$NR^cR^d$,
where:
$R^c$ is a $C_1$-$C_{12}$alkyl and $R^d$ is H or a $C_1$-$C_{12}$alkyl; or $R^c$ and $R^d$ are taken together with the N to which they are attached to form a heterocyclic ring;
$R^2$ is hydrogen, halo, nitro, alkyl and substituted alkyl and
$R^4$ is independently H, alkyl, aryl
or a pharmaceutically acceptable salt thereof.
2. The compound of claim 1, or a pharmaceutically acceptable salt thereof, where $R^2$ is hydrogen.
3. The compound of claim 2, or a pharmaceutically acceptable salt thereof, where at least one of (i)-(v) applies: (i) $W^1$ is CN; (ii) $W^2$ is perhaloalkyl; (iii) $Z^1$ is S; (iv) $Z^2$ is O; and (v) $Y^1$ and $Y^2$ are both methyl.
4. A compound of formula I:

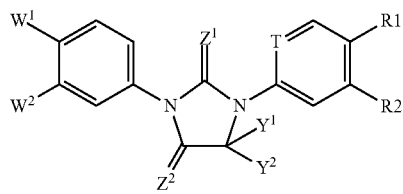

wherein
$W^1$ is CN, $NO_2$ or $SO_2R^4$;
$W^2$ is alkyl, substituted alkyl, alkenyl, substituted alkenyl, alkynyl, substituted alkynyl or halogen;
$Z^1$ is S or O;
$Z^2$ is S, O or $NR^4$;
$Y^1$ and $Y^2$ are independently hydrogen, alkyl, substituted alkyl, alkenyl, substituted alkenyl, alkynyl, substituted alkynyl, aryl, substituted aryl, heteroaryl, substituted heteroaryl, arylalkyl, arylalkenyl, arylalkynyl, heteroaralkyl, heterocyclyl, or substituted heterocyclyl; or $Y^1$ and $Y^2$ are connected to form a cycle which can be heterocyclic, substituted heterocyclic, cycloalkyl, or substituted cycloalkyl;

T is nitrogen and can be at any position in the ring;

$R^1$ is —$C_1$-$C_8$alkyl-$NR^aR^b$, —O—$C_1C_8$alkyl-$NR^cR^d$ or —C(O)$NR^eR^f$, where:

$R^a$ is a $C_1$-$C_{12}$alkyl and $R^b$ is H or a $C_1$-$C_{12}$alkyl; or $R^a$ and $R^b$ are taken together with the N to which they are attached to form a heterocyclic ring;

$R^c$ is a $C_1$-$C_{12}$alkyl and $R^d$ is H or a $C_1$-$C_{12}$alkyl or $R^c$ and $R^d$ are taken together with the N to which they are attached to form a heterocyclic ring;

$R^e$ and $R^f$ are taken together with the N to which they are attached to form a heterocyclic ring;

$R^2$ is hydrogen, halo, nitro, alkyl and substituted alkyl and $R^4$ is independently H, alkyl, aryl, or a pharmaceutically acceptable salt thereof, wherein at least one of (i)-(v) applies; $W^1$ is CN; (ii) $W^2$ is perhaloalkyl; (iii) $Z^1$ is S; (iv) $Z^2$ is O; (v) $Y^1$ and $Y^2$ are both methyl.

5. A compound of formula (I):

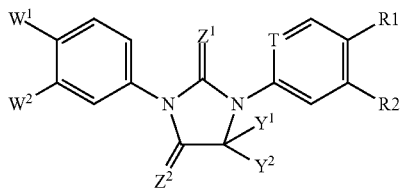

wherein:

$W^1$ Is CN, $NO_2$ or $SO_2R^4$;

$W^2$ is alkyl, substituted alkyl, alkenyl, substituted alkenyl, alkynyl, substituted alkynyl or halogen;

$Z^1$ is S or O;

$Z^2$ is S, O or $NR^4$;

$Y^1$ and $Y^2$ are independently hydrogen, alkyl, substituted alkyl, alkenyl, substituted alkenyl, alkynyl, substituted alkynyl, aryl, substituted aryl, heteroaryl, substituted heteroaryl, arylalkyl, arylalkenyl, arylalkynyl, heteroaralkyl, heterocyclyl, or substituted heterocyclyl; or $Y^1$ and $Y^2$ are connected to form a cycle which can be heterocyclic, substituted heterocyclic, cycloalkyl, or substituted cycloalkyl;

T is carbon or nitrogen and can be at any position in the ring;

$R^1$ is —O—$C_1$-$C_8$alkyl-$NR^cR^d$, where:

$R^c$ is a $C_1$-$C_{12}$alkyl and $R^d$ is H or a $C_1$-$C_{12}$alkyl or $R^c$ and $R^d$ are taken together with the N to which they are attached to form a heterocyclic ring;

$R^2$ is hydrogen, halo, nitro, alkyl or substituted alkyl and $R^4$ is H, alkyl, or aryl, or a pharmaceutically acceptable salt thereof.

6. The compound of claim 5, or a pharmaceutically acceptable salt thereof, where $R^2$ is halo.

7. The compound of claim 6, or a pharmaceutically acceptable salt thereof, where at least one of (i)-(vi) applies: (i) $W^1$ is CN; (ii) $W^2$ is perhaloalkyl; (iii) $Z^1$ is S; (iv) $Z^2$ is O; (v) $Y^1$ and $Y^2$ are both methyl and (vi) T is C.

8. The compound of claim 5, or a pharmaceutically acceptable salt thereof, where $R^2$ is hydrogen.

9. A pharmaceutical composition comprising a compound of claim 1 or a pharmaceutically acceptable salt thereof and a pharmaceutically acceptable carrier.

10. A pharmaceutical composition comprising a compound of claim 4 or a pharmaceutically acceptable salt thereof and a pharmaceutically acceptable carrier.

11. A pharmaceutical composition comprising a compound of claim 5 or a pharmaceutically acceptable salt thereof and a pharmaceutically acceptable carrier.

12. A method of treating prostate cancer in an individual in need thereof comprising administering to the individual an effective amount of a compound of claim 1 or a pharmaceutically acceptable salt thereof.

13. The method of claim 12, where the individual has castration-resistant prostate cancer.

14. The method of claim 12, where the individual has hormone-sensitive prostate cancer.

15. A method of treating prostate cancer in an individual in need thereof comprising administering to the individual an effective amount of a compound of claim 4 or a pharmaceutically acceptable salt thereof 16. The method of claim 15, where the individual has castration-resistant prostate cancer.

17. The method of claim 15, where the individual has hormone-sensitive prostate cancer.

18. A method of treating prostate cancer in an individual in need thereof comprising administering to the individual an effective amount of a compound of claim 5 or a pharmaceutically acceptable salt thereof.

19. The method of claim 18, where the individual has castration-resistant prostate cancer.

20. The method of claim 18, where the individual has hormone-sensitive prostate cancer.

* * * * *